(12) United States Patent  (10) Patent No.: US 8,899,230 B2
Immel  (45) Date of Patent: Dec. 2, 2014

(54) AEROSOL THERAPY DEVICE WITH HIGH FREQUENCY DELIVERY

(75) Inventor: Timothy Sean Immel, Santa Barbara, CA (US)

(73) Assignee: Nasologix, Inc., Newbury Park, CA (US)

( * ) Notice: Subject to any disclaimer, the term of this patent is extended or adjusted under 35 U.S.C. 154(b) by 874 days.

(21) Appl. No.: 12/867,379

(22) PCT Filed: Feb. 13, 2009

(86) PCT No.: PCT/US2009/034092
§ 371 (c)(1),
(2), (4) Date: Feb. 10, 2011

(87) PCT Pub. No.: WO2009/102976
PCT Pub. Date: Aug. 20, 2009

(65) Prior Publication Data
US 2011/0120456 A1 May 26, 2011

Related U.S. Application Data

(60) Provisional application No. 61/029,224, filed on Feb. 15, 2008.

(51) Int. Cl.
*A61M 15/08* (2006.01)
*A61M 15/00* (2006.01)

(52) U.S. Cl.
CPC ........... *A61M 15/08* (2013.01); *A61M 15/0085* (2013.01); *A61M 15/0098* (2013.01)
USPC ............. 128/203.15; 128/203.12; 128/200.14

(58) Field of Classification Search
CPC .......... A61M 15/0085; A61M 15/009; A61M 15/08; A61M 2005/31598; A61M 2015/0098; A61M 2025/0008; A61M 2202/064; A61M 2202/097; A61M 2205/054; A61M 2205/7545; A61M 25/0105; A61M 25/10; A61M 31/00; A61M 39/223; A61M 5/14276; A61M 5/1782; A61M 5/19; A61M 5/3145; A61M 5/31596
USPC ............. 128/200.24, 200.26, 203.12, 203.14, 128/203.15, 203.22, 204.18, 204.23, 128/207.13, 207.18
See application file for complete search history.

(56) References Cited

U.S. PATENT DOCUMENTS 4,699,136 A * 10/1987 Krauser .................... 128/203.22
6,058,932 A * 5/2000 Hughes .................... 128/200.24

(Continued)

FOREIGN PATENT DOCUMENTS

DE    102 39 321 B3    4/2004
EP    0 507 707 A1    10/1992

(Continued)

OTHER PUBLICATIONS

CA 2,715,302 Office Action mailed Oct. 9, 2012.

(Continued)

*Primary Examiner* — Annette Dixon
(74) *Attorney, Agent, or Firm* — Wilson Sonsini Goodrich & Rosati

(57) ABSTRACT

The present invention relates to an aerosol therapy device, wherein an aerosol is generated in an aerosol generating device and is supplied through a nosepiece to a patient's nasal cavities via a single pulsed main aerosol flow.

41 Claims, 9 Drawing Sheets

(56) References Cited

U.S. PATENT DOCUMENTS

| | | | |
|---|---|---|---|
| 6,325,475 B1 * | 12/2001 | Hayes et al. | 347/2 |
| 7,225,807 B2 | 6/2007 | Papania et al. | |
| 7,435,252 B2 * | 10/2008 | Krespi et al. | 607/88 |
| 7,449,173 B2 * | 11/2008 | Rabinowitz et al. | 424/45 |
| 8,146,589 B2 * | 4/2012 | Djupesland | 128/203.18 |
| 8,402,969 B2 * | 3/2013 | Gabriel et al. | 128/204.23 |
| 2003/0024526 A1 * | 2/2003 | Ganan-Calvo | 128/200.14 |
| 2004/0084050 A1 * | 5/2004 | Baran | 128/207.14 |
| 2005/0150489 A1 * | 7/2005 | Dunfield et al. | 128/200.14 |
| 2005/0244339 A1 | 11/2005 | Jauernig et al. | |
| 2006/0162722 A1 | 7/2006 | Boehm et al. | |
| 2007/0202051 A1 * | 8/2007 | Schuschnig | 424/45 |

FOREIGN PATENT DOCUMENTS

| | | |
|---|---|---|
| EP | 1 818 070 | 8/2007 |
| WO | WO 97/17933 | 5/1997 |
| WO | WO97/17933 | 5/1997 |
| WO | WO2004/050139 | 6/2004 |
| WO | WO 2004/050139 | 6/2004 |

OTHER PUBLICATIONS

"Eindringvermogen von Aerosolen in Nebenraume", H. Kauff, Archiv. Klin. Exper. Ohren-, Nasen- and Kehlkopfheilk. 190, 95-108 (1968).

PCT/US2009/34092 International Search Report mailed Sep. 23, 2009.

PCT/US2009/34092 Written Opinion mailed Sep. 23, 2009.

PCT/US2009/34092 International Report on Patentability mailed Aug. 17, 2010.

EP09710824.5 Extended EP Search Report dated May 21, 2014.

* cited by examiner

3(A)

3(B)

3(C)

4(A)

4(B)

4(C)

5(A)

5(B)

5(C)

6(A)

6(B)

6(C)

AEROSOL THERAPY DEVICE WITH HIGH FREQUENCY DELIVERY

CROSS REFERENCE TO RELATED APPLICATIONS

This application claims the benefit of U.S. Provisional Application No. 61/029,224, entitled, "Aerosol Therapy Device with High Frequency Delivery," filed Feb. 15, 2008, which is incorporated herein by reference in its entirety.

BACKGROUND OF THE INVENTION

The present invention relates to an aerosol therapy device, wherein an aerosol is generated in an aerosol generating device and is supplied through a nosepiece to a patient's nasal cavities via a single pulsed main aerosol flow.

The four paranasal sinuses (maxillary, sphenoid, frontal and ethmoid) develop as outpouchings of the nasal mucosa. At birth, they are fluid filled and pneumatization occurs gradually during childhood so that by the age of about 16 years all sinuses are generally fully developed. The sinuses remain connected to the nasal cavity via narrow ostia with a lumen diameter of 1 to 3 mm. The ostia of the frontal, maxillary and anterior ethmoid sinuses open to the osteomeatal complex. The osteomeatal complex is important because the frontal, ethmoid and maxillary sinuses all drain through this area. Thus, ostial patency is necessary for adequate ventilation of the sinuses and the penetration of an aerosol through the ostia to result in aerosol deposition within the paranasal sinuses.

Studies using various models of the human nose have demonstrated that when current aerosol therapy devices are used for sinunasal therapy, aerosol deposition in the paranasal sinuses is less than expected and desired. One contributing factor to the difficulties of current nebulized sinunasal therapies in achieving adequate aerosol deposition is the anatomical features of the paranasal sinuses. As described supra, the opening size of the ostia, which is very small, also has a great influence on aerosol deposition.

Due to its anatomical structure, it is thought that the sinus cavity behaves like a kind of Helmholtz resonator, which is a container of gas with an open hole at the end of a neck. Such a container has a specific resonance frequency wherein the air within the neck (airplug) will be most easily moved. An outside variation in air pressure causes the air plug in the neck (i.e., the ostia of the sinuses) to oscillate in and out. Thus, by oscillating the ostia at the appropriate frequency, one is able to increase gas exchange via the ostia.

As shown in "Eindringvermogen von Aerosolen in Nebenraume", H. Kauff, Archiv. Klin. Exper. Ohren-, Nasen- and Kehlkopfheilk. 190, 95-108 (1968), the use of pressure oscillations and co-vibrations can cause aerosols to penetrate the paranasal sinuses, through which the main aerosol flow through the nasal cavities does not otherwise actively flow. An example of these effect is known from EP 0 507 707 A1. According thereto, an aerosol flow is superimposed with pressure fluctuations which are supposed to cause the aerosol particles/droplets in the main aerosol flow to pass through the ostia and enter the paranasal sinuses. In this way, even though the main aerosol flow does not directly flow through the paranasal sinuses, they can be reached and treated by a drug administered in aerosol form. As also with other types of aerosol therapy, it is attempted to deposit sufficient quantities of the drug at the desired points, for which in the case of the paranasal sinuses a sufficient quantity of the aerosol of the main aerosol flow must pass through the ostia and penetrate the paranasal sinuses.

DE 102 39 321 B3 provides an aerosol therapy device of the type described above, comprising a nebulizer having an aerosol generator to which compressed air is supplied for the generation of a main aerosol flow and having a connector for supplying pressure fluctuations which are superimposed on the main aerosol flow, and a nosepiece for supplying the aerosol to one of the two alae of the nose, which is connected to the nebulizer. A flow resistance device is furthermore provided, by means of which the flow resistance at the other of the two alae of the nose of the user is precisely defined. Owing to the flow resistance at the other nostril, the superimposed pressure fluctuations cause to a greater extent the aerosol of the main aerosol flow to also reach the paranasal sinuses and deposition of the aerosol there.

However, the supply of the flow of compressed gas and pressure fluctuations described in DE 102 39 321 B3 requires a specific design of the nebulizer, and thus not every nebulizer is suitable for this use.

Also of interest to the present invention is the treatment of diseases by delivering neurologic agents to the brain or central nervous system (CNS). Many drugs are not being effectively and efficiently delivered to the brain or CNS using conventional drug delivery system. Therapeutic treatment of various CNS disorders has been difficult to achieve because of the failures of drug delivery systems which target the CNS. Contributing factors to the difficulty include insufficient blood brain barrier penetration, rapid peripheral metabolism, poor intestinal absorption, inability to use synthetic precursors, and untoward side effects.

Particularly, the impermeability of the blood vessels of the brain referred to collectively as the blood-brain barrier (BBB) has posed difficulties. The blood vessels of the brain are unique when compared to the blood vessels found in the periphery of the body. Tight apposition of BBB endothelial cells (EC) to neural cells like astrocytes, pericytes and neurons induces phenotypic features that contribute to the observed impermeability. Tight junctions between ECs comprising the BBB limit paracellular transport, while the lack of pinocytotic vesicles and fenestrae limit non-specific transcellular transport. The tight junctures between endothelial cells in brain results in a very high trans-endothelial electric resistance of 1500-2000 W $cm^2$ compared to 3-33 W $cm^2$ of other tissues. These factors combine to restrict molecular flux from the blood to the brain to those molecules that are less than 500 Daltons and also lipophilic. Thus, using the large mass transfer surface area (over 21 $m^2$ from 400 miles of capillaries in human brain) of the bloodstream as a delivery vehicle is largely infeasible except in those circumstances where a drug with the desired pharmacological properties fortuitously possesses the size and lipophilicity attributes allowing it to pass freely through the blood vessel. Because of such restrictions, it has been estimated that greater than 98% of all small molecule pharmaceuticals and nearly 100% of the emerging class of protein and gene therapeutics do not cross the BBB.

Intranasal drug delivery is of particular interest, as the brain and nose compartments are connected to each other via the olfactory route and via peripheral circulation. Studies have indicated ultrasound as a means to temporarily disrupt the BBB, thus allowing targeted drug delivery to the CNS. Since existing methods of delivery to the olfactory system have shown limited delivery, the present invention provides means to effectively deliver neurologic agents to the brain.

In view of the difficulties associated with current nebulization therapies in achieving aerosol deposition in the paranasal sinuses and CNS, the object of the present invention is to provide increased aerosol delivery and deposition in the paranasal sinuses and/or CNS via an aerosol therapy device wherein an aerosol is generated and supplied through to a patient's nasal cavities via a single pulsed main aerosol flow.

SUMMARY OF THE INVENTION

The present invention addresses the inadequacies of current sinunasal nebulization therapies by providing an aerosol therapy device which can provide increased aerosol delivery of an active agent to the paranasal sinuses via the aerosol delivery of the active agent with a pulsating flow of air comprising a pressure field which, acting under the principles described above related to the Helmholtz resonator, results in increased aerosol penetration through the ostia of the sinus and increase aerosol deposition within the paranasal cavity. In certain aspects, the active agent comprises an active pharmaceutical ingredient. In other aspects, the active agent is a substance or chemical that is generally regarded as safe but does not comprise an active pharmaceutical ingredient.

In other embodiments, the aerosol therapy device described herein can provide increase aerosol delivery of an active agent to the nasal passages and/or sinuses for the topical delivery of an active agent to a patient in need thereof. In still other embodiments, the aerosol therapy device described herein can provide increase aerosol delivery of an active agent to the nasal passages and/or sinuses for the systemic delivery of an active agent to a patient in need thereof. In yet other embodiments, the aerosol therapy device described herein can provide increase aerosol delivery of an active agent to the olfactory region of the nasal passages for the delivery of an active agent to the central nervous system of a patient in need thereof. In certain aspects, the active agent comprises an active pharmaceutical ingredient. In other aspects, the active agent is a substance or chemical that is generally regarded as safe but does not comprise an active pharmaceutical ingredient.

In certain embodiments, the present invention can comprise an aerosol therapy device for the delivery of an active agent to the paranasal sinuses wherein the aerosol therapy device comprises an aqueous drug reservoir, the aqueous drug reservoir being connected to an aerosol generator for the generation of an aerosol particles, the aerosol generator being connected to an air-flow supply device, the air-flow supply device producing a single airflow to carry the aerosol particles, wherein the single airflow consists of a pulsating flow of air and comprises an acoustic pressure field produced by a pulsed pressure wave, wherein said pulsating airflow pulsates at a frequency greater than 100 Hz and a nosepiece to direct the single airflow comprising aerosol particles into one of the two alae of the nose wherein the device delivers the aerosol particles of the active agent to the paranasal sinuses. In certain embodiments, the device can comprise a twin-port nose piece. In certain aspects, the active agent comprises an active pharmaceutical ingredient. In other aspects, the active agent is a substance or chemical that is generally regarded as safe but does not comprise an active pharmaceutical ingredient.

In other aspects, the present invention can comprise an aerosol therapy device for intranasal delivery of an active agent to the central nervous system via the olfactory region of the nasal passages to a patient in need thereof comprising an aqueous drug reservoir, the aqueous drug reservoir being connected to an aerosol generator for the generation of aerosol particles of an active agent, the aerosol generator being connected to an air-flow supply device, the air-flow supply device producing a single airflow to carry the aerosol particles of an active agent, wherein said single airflow consists of a pulsating flow of air and comprises a pressure field produced by a pulsed pressure wave; and a twin-port nosepiece to simultaneously direct the single airflow comprising aerosol particles of into both alae of the nose, whereby said aerosol therapy device intranasally delivers aerosol particles comprising an active agent to the olfactory region of the nasal passages. In certain aspects, the active agent comprises an active pharmaceutical ingredient. In other aspects, the active agent is a substance or chemical that is generally regarded as safe but does not comprise an active pharmaceutical ingredient.

In yet other aspects, the present invention can comprise an aerosol therapy device for systemic delivery of an active agent to the nasal passages and/or sinuses of a patient in need thereof comprising: an aqueous drug reservoir, the aqueous drug reservoir being connected to an aerosol generator for the generation of aerosol particles of an active agent, the aerosol generator being connected to an air-flow supply device, the air-flow supply device producing a single airflow to carry the aerosol particles of an active agent, wherein the single airflow consists of a pulsating flow of air and comprises a pressure field produced by a pulsed pressure wave; and a nosepiece to direct said single airflow comprising aerosol particles of into one or both alae of the nose, whereby said aerosol therapy device delivers aerosol particles comprising an active agent to the nasal passages and/or sinuses. In certain aspects, the active agent comprises an active pharmaceutical ingredient. In other aspects, the active agent is a substance or chemical that is generally regarded as safe but does not comprise an active pharmaceutical ingredient.

In the present invention, an aerosol comprising an active agent is delivered to the nasal cavity by an aerosol therapy device which comprises an air flow supply device that simultaneously and/or concurrently generates high frequency pulses of air which consists of oscillating pressure fields. In certain embodiments, the pressure field is an acoustic pressure field. The pulsated air flow which carries the aerosol may be generated in various forms of actuators (e.g. air flow supply device and/or pump).

In certain embodiments, the air flow supply device or pump can be driven by a piezoelectric or piezoceramic element, for example a crystal in a shape of a disk. The deformation causes the resonant acoustic cavity adjacent to the piezoelectric disk to generate a pressure sound field confined within the air flow supply device. The same pumping function can be used to generate a convective flow through an air outlet, thereby delivering a pulsated airflow to carry the aerosol to the nasal cavity.

In other embodiments, the air flow supply device or pump can be driven by a shape memory alloy such as a nickel-titanium alloy coil, a thermopneumatic pump such as a thin-film resistive heater put inside an air cavity with a diaphragm membrane, a magnetostrictive disk, an electromagnetic system such as a Ni—Fe valve or a solenoid, an electrostatic system, a bimetallic system, or an electro-active polymer (EAP) disk.

In yet still other embodiments, a mechanically driven diaphragm pump creates a pulsated air flow comprising an oscillating pressure field. In one embodiment, the pressure fluctuation is generated by a piston rod attached to a diaphragm membrane, which seals a hollow space (pressure chamber) which will generate the acoustic sound field. In this embodiment, the piston rod can be supported eccentrically on a driving pulley so that the piston rod causes a pressure-fluctuation-generating movement of the membrane when the driving pulley turns. In another embodiment, diaphragm membrane is actuated by a pneumatic cylinder with a solenoid or servo valve as a pneumatic controller. In yet another embodiment, the cylinder can be a hydraulic cylinder fed by hydraulic fluid under the control of a servo valve and hydraulic pump.

In still other embodiments, a pneumatic pump without a mechanical shaft can be used, such as a pneumatic drive directly generating movement of the diaphragm membrane or a piston. In yet other embodiments, a hydraulic drive can directly create the diaphragm membrane movement by hydraulic fluid. In other embodiments, a turbine can be used to generate the pulsated air flow or in conjunction with the pneumatic and hydraulic pumps described above.

As described herein, the pulsated flow of air from the air flow supply device and/or pump is used to carry the aerosol into the patient's nasal cavity within a defined oscillating pressure field. In certain embodiments, the air flow supply device comprises an active or passive check valve or multiple check valves to prevent back flow, such as a ball valve, flapper valve, nozzle-flapper valve, or solenoid. In other embodiments, the air flow supply device is valve-less and can comprise a diffuse/nozzle or an unsymmetrical corrugation chamber bottom (UCCB) to create the positive air flow.

In yet still other embodiments, a peristaltic pump such as a roller or centrifugal pumps can be used to obtain the pulsated air flow, thereby removing the need for a check valve or diffuse/nozzle element. In other embodiments, a single piston pump or a rapid refill pump can be used. In certain other embodiments, a rotary pump or a rotary piston pump can be used.

In still other embodiments, the pulsated air flow can be generated by spinning a disc comprising different cut openings. In this embodiment, altering the size of the cut openings, the location or orientation of the cut openings, the quantity of cut openings, and/or rpm of the controlled motor one can control the pulse frequency and/or pressure of the air flow from an air reservoir.

In certain embodiments, the air flow supply device provides a pulsated flow of air having a pulse frequency of greater than 100 Hz. In certain embodiments the pulse frequency can comprise the ultrasonic range from about 150 Hz to about 20 KHz. In certain other embodiments, the pulse frequency can be from about 150 Hz to about 10 KHz. In certain other embodiments, the pulse frequency can be selected to achieve the Helmholtz resonator frequency of the sinuses, which typically ranges from about 150 to about 6000 Hz. In certain embodiments, the pulse frequency can be selected to achieve the Helmholtz resonator frequency of the sinuses at a range from about 300 to about 4000 Hz. In certain other embodiments, the pulse frequency can be selected to achieve the Helmholtz resonator frequency of the sinuses at a range from about 150 to about 2500 Hz. In still other embodiments, the pulse frequency can be selected to achieve the Helmholtz resonator frequency of the sinuses at a range about 500 to about 3000 Hz. In one embodiment, the airflow pulsates at a frequency from about 200 Hz to about 10 KHz. In another embodiment, airflow pulsates at a frequency from about 300 Hz to about 4000 Hz. In yet another embodiment, airflow pulsates at a frequency from about 500 Hz to about 3000 Hz. In other embodiments, the pulse frequency can be adjusted to the typical Helmholtz resonator frequency of a particular sinus, thereby achieving selective aerosol delivery to a particular sinus. Various means of altering the frequency is known to one skilled in the art.

In certain embodiments, the air flow supply device provides a pulsated flow of air to achieve optimum deposition of the active agent to the CNS through the olfactory route. In certain embodiments, the range of useful frequencies can be from about 1 Hz to about 20 KHz. In other embodiments, the frequency can be from about 1 Hz to about 10 KHz. In yet other embodiments, the frequency can be from about 100 Hz to about 1 KHz. In yet still other embodiments, the frequency can be from about 300 Hz and about 700 kHz. In other embodiments, the frequency can be from about 10 Hz to about 100 Hz.

In other embodiments, the pressure field can be produced by a conventional audio amplifier and speaker set. In still other embodiments, the conventional audio amplifier and speaker set is used in conjunction with the pulsated flow from the air flow supply device described. In certain embodiments, the pressure field is an acoustic pressure field.

In yet other embodiments, the device can have self-tuning capabilities. Self-tuning to the resonant frequency can be achieved by any means known to one skilled in the art. In certain embodiments, the pulse frequency can be swept across the typical optimum frequency range of each of the four paranasal sinuses at the initiation of patient treatment, thereby providing targeted delivery of the aerosol to each of the paranasal sinuses. In certain embodiments, the Helmholtz frequency of a person can be determined before treatment and the range of frequencies would be centered at this frequency. In still other embodiments, the sweeping function is used in conjunction with the self-tuning function. In certain embodiments, a microphone is within the nosepiece such that it is positioned near or inside the patient's nasal cavity to measure the frequency, which in turn is used for the self-tuning.

The pressure of the air flow is adjusted to reach optimum sinus deposition. With the use of higher frequencies, the delivery pressure can be reduced without significant loss in sinus deposition. In certain embodiments, the pressure can be about 5 to about 50 mbar. In other embodiments, the pressure can be about 15 to about 40 mbar. In yet other embodiments, the pressure can be about 15 to about 25 mbar. Even higher amplitudes than about 50 mbar can be useful for certain patients and indications in which some degree of discomfort to the patients may be found acceptable, such as serious diseases and affections of the sinus mucosa. In another embodiment, a safety valve is equipped to prevent overpressure of the nasal cavity.

In certain embodiments, the aerosol therapy device described herein can comprise a twin-port nosepiece to direct the single airflow comprising aerosol particles into one of the two alae of the nose. The nosepiece is shaped to obtain an air tight seal at the alae of the nose. In certain embodiments, the ends to be inserted into the alae can take the shape of a truncated cone with an aperture angle in a range of from 10° to 80°. In other embodiments, the aperture angle can be in a range of 20° to 60°. In yet other embodiments, the aperture angle can be in a range of 30° to 40°. In yet still other embodiments, the aperture angle can be in a range of 40° to 70°. In other embodiments, the ends to be inserted can take the shape of a bulb. In certain embodiments, the ends to be inserted can be connected with a centerpiece. In other embodiments, side shields can be provided for better fit and tighter seal. In certain other embodiments, the ends to be inserted into the alae can comprise an inflatable balloon device comprising a truncating cone shape when inflated.

In certain embodiments, the aerosol can be delivered to both alae simultaneously by a twin-port nosepiece. In other embodiments, the aerosol flow can be alternated between the alae, delivering the aerosol to one of the two alae at a time. In certain embodiments, the flow to each ala is carried out in intervals ranging from 1 second intervals to two minute intervals. In one embodiment, the flow to each ala is carried out in 1 second intervals (e.g., for the intranasal delivery of a vaccine). In another embodiment, the flow to each ala is carried out in 5 second intervals. In yet another embodiment, the flow to each ala is carried out in 10 second intervals. In another embodiment, the flow to each ala is carried out in 15 second intervals. In still another embodiment, the flow to each ala is carried out in 30 second intervals. In yet another embodiment, the flow to each ala is carried out in 45 second intervals. In still yet another embodiment, the flow to each ala is carried out in 1 minute intervals. In yet still another embodiment, the flow to each ala is carried out in two minute intervals. Various means for altering the flow direction can be recognized by one skilled in the art, such as use of a manual switch, a mechanical valve, an electromechanical valve, a diaphragm valve, pneumatic actuators or hydraulic actuators. In yet other embodiments, a microprocessor can be used in conjunction to alter the parameters such as the delivery time interval. In still other embodiments, the means for altering the flow direction can be controlled to provide for a slight opening to remain the "closed" nosepiece port to generate back pressure if desired.

As described herein, the aerosol can be generated by any aerosol or vapor generating device known in the art, e.g., a pneumatic or jet nebulizer-type device. In this embodiment, compressed gas can be used to disperse a liquid into a fine mist. In certain embodiments, the aerosol can be generated by an ultrasonic device. In certain embodiments, the aerosol generator can be a pulsating membrane device, a device comprising a vibrating mesh or plate with multiple apertures, a thin-film resistive heater with a diaphragm membrane, or a device comprising a vibration generator. In certain other embodiments, the vibration is provided by a piezoelectric actuator activated by an electronic drive circuit. In other embodiments, the vibration is provided by magnetostrictive actuation, microelectromechanical actuation, electromagnetic actuation, electric field actuation such as capacitive actuators, or Coulombic actuation.

In certain embodiments, the perforate membrane is a mesh or thin plate with many laser-drilled holes as the nozzles. In certain other embodiments, the perforate membrane further comprises geometry to achieve a plume angle such that the aerosol flows to the nosepiece with minimal obstruction. In other embodiments, the perforate membrane is ceramic (including zirconate PZT), stainless steel, gold, silver, copper, zinc, aluminum, or any other combination thereof. In yet other embodiments, the aerosol is generated by a thermal vaporizer comprising a heating element or multiple heating elements.

As describe herein, the droplet diameter of the aerosols produced by the aerosol generator can be tailored to a particular application by altering the diameter of the laser-drilled holes. In certain embodiments described herein, the holes have a taper. In certain other embodiments, the aerosol size is adjusted by altering the temperature of the heating element or elements of the thermal vaporizer. In other embodiments, the aerosol particles produced by the aerosol generator can have a mass median aerodynamic diameter (MMAD) of about 0.5 µm to about 150 µm. In other embodiments, the aerosol particles produced by the aerosol generator can have a mass median aerodynamic diameter (MMAD) of about 0.5 µm to about 10 µm. In certain other embodiments, the aerosol particles produced by the aerosol generator can have a MMAD of about 2 µm to about 8 µm. In still other embodiments, the aerosol particles produced by the aerosol generator can have a MMAD of about 3 µm to about 5 µm. In still other embodiments, the aerosol particles produced by the aerosol generator can have a MMAD of about 3 µm to about 10 µm. In still other embodiments, the aerosol particles produced by the aerosol generator can have a MMAD of about 1 µm to about 5 µm. In still other embodiments, the aerosol particles produced by the aerosol generator can have a MMAD of about 1 µm to about 30 µm. In still other embodiments, the aerosol particles produced by the aerosol generator can have a MMAD of about 1 µm to about 20 µm. In still other embodiments, the aerosol particles produced by the aerosol generator can have a MMAD of about 1 µm to about 15 µm. In still other embodiments, the aerosol particles produced by the aerosol generator can have a MMAD of about 1 µm to about 10 µm. In still other embodiments, the aerosol particles produced by the aerosol generator can have a MMAD of about 10 µm to about 30 µm. In still other embodiments, the aerosol particles produced by the aerosol generator can have a MMAD of about 10 µm to about 20 µm. In yet other embodiments, the aerosol particles produced by the aerosol generator can have a MMAD of about 5 µm to about 20 µm. In yet still other embodiments, the aerosol particles produced by the aerosol generator can have a MMAD of about 20 µm to about 150 µm. In still other embodiments, the aerosol particles produced by the aerosol generator can have a MMAD of about 20 µm to about 50 µm. In other embodiments, the aerosol particles produced by the aerosol generator can have a MMAD of about 50 µm to about 150 µm.

As described herein, the aerosol therapy device comprises a drug reservoir into which the aqueous drug is placed into prior to aerosolization. The drug reservoir is connected to the aerosol generator such that the aqueous drug to be delivered via the aerosol therapy device is fed to the aerosol generator. In certain embodiments, the aqueous drug can be directly poured into a reservoir adjacent to the aerosol generator or transferred by an aspirator. In other embodiments, the aqueous drug can be provided in a disposable containers filled with individual doses, such as an ampoule or vial, which can be connected to a mated fitting of the reservoir, such as a luer, a cartridge or screw fitting. In certain other embodiments, a lock and key function such as radio frequency identification (RFID) system or encrypted microchip is provided, wherein the disposable container provides the delivery device information such as the drug type and optimal delivery parameters (e.g., pressure, pulsing frequency, back pressure and duration of administration time for each nasal) for the particular drug and indications of use.

In certain other embodiments, the aerosol generator forms a part of the wall of the liquid storage container so that an aqueous drug within the liquid storage container directly contacts the aerosol generator, thereby ensuring continuous aerosol generation. In certain embodiments, the aqueous drug in the reservoir is driven to the diaphragm by gravity. In certain other embodiments, a tube is used to drive the aqueous drug to the diaphragm by capillary action. In certain embodiments, a positive pressure can be applied to the drug reservoir to facilitate delivery of the aqueous drug to the aerosol generator.

In certain embodiments, the aerosol therapy device comprises a drug reservoir which can accommodate an aqueous solution having a volume of about 10 mL or less. In one embodiment, the drug reservoir can accommodate an aqueous solution having a volume of about 5 mL or less. In another embodiment, the drug reservoir can accommodate an aqueous solution having a volume of about 4 mL or less. In yet another embodiment, the drug reservoir can accommodate an aqueous solution having a volume of about 3 mL or less. In still another embodiment, the drug reservoir can accommodate an aqueous solution having a volume of about 2 mL or less. In yet still another embodiment, the drug reservoir can accommodate an aqueous solution having a volume of about 1 mL or less.

In certain embodiments, the aerosol therapy device described herein can be turned on by the user manually while the soft palate is closed by the patient, ensuring minimal delivery of the aerosol to the lungs and increases the potential for aerosol deposition in the sinuses.

In certain embodiments, the aerosol generator and pulsated air generator are triggered when the patient breathes into an exhalation triggering device. In certain embodiments, the exhalation triggering device further comprises of a mouthpiece that can be fixed or removable. In other embodiments, a restrictor is positioned to control the exhalation rate such as a hole in the mouthpiece or a flow restrictor inside the exhalation pathway with a one way valve allowing for ease of inhalation. In certain aspect of the present invention, the breath trigger or breath actuator can comprise a sensor for detecting any suitable parameter such as gas flow, pressure, temperature, sound, moisture, carbon dioxide concentration and oxygen concentration. Many suitable sensors are envisaged including the use of optical sensors, mechanical sensors, flow transducers, thermal sensors, gas detectors, and motion detectors. The signal from the exhalation triggering device is transmitted to the aerosol therapy device for actuation. In certain embodiments, the signal is transmitted to an electronic data management system, further comprising a microprocessor and predictive algorithm or look-up table, which then controls the aerosol therapy device.

In certain embodiments of the aerosol therapy device described herein, the aerosol therapy device can deliver the aqueous solution comprising the active agent in about 10 minutes or less. In one embodiment, the aerosol therapy device can deliver the aqueous solution comprising the active agent in about 5 minutes or less. In another embodiment, the aerosol therapy device can deliver the aqueous solution comprising the active agent in about 4 minutes or less. In yet another embodiment, the aerosol therapy device can deliver the aqueous solution comprising the active agent in about 3 minutes or less. In still another embodiment, the aerosol therapy device can deliver the aqueous solution comprising the active agent in about 2 minutes or less.

The aerosol therapy device described herein can be used to deliver a variety of different active agents. Any drug that can be provided in a solution, dispersion, emulsion, colloidal liquid, micelle or mixed micelle liquid, liposomal liquid, nanosuspension, or a suspension can be delivered as an active agent via the aerosol therapy device set forth herein, which offers the possibility of topical drug delivery to the nasal mucosa and/or systemic drug delivery via the nasal sinuses, depending on the particle size distribution achieved. In certain embodiments, the aerosol therapy device described herein can be used to deliver neurologic agents to the brain or central nervous system to treat disorders or diseases of neurological etiology. In still other embodiments, the aerosol therapy device described herein can be used to deliver vaccines designed for aerosol and/or nasal delivery for the prevention of certain diseases or disorders including, but not limited to, influenza, tuberculosis, measles, and HIV/AIDS.

Examples of diseases that can be treated by the use of the present invention includes, but are not limited to, acute and chronic sinusitis, acute and chronic rhinitis, acute and chronic rhinosinusitis, allergic rhinitis, symptoms related to the common cold (e.g., nasal congestion and pyrexia), endocrine and metabolic disorders, migraines, sleep disorders, autoimmune diseases, osteoporosis, pain, nausea and vomiting, neurological diseases and disorders, obesity, sexual dysfunctions, cardiovascular diseases and episodes, nasal polyps, nasal furuncles, epistaxis, wounds of the nasal or sinunasal mucosa, dry nose syndrome, nasal or paranasal disease, nasal bleeding, herpes, sarcoidosis, fibrosis, cancer, autoimmune reaction, and other diseases of the upper and lower respiratory tract.

In certain embodiments, the surface tension of the aqueous drug can be between about 10 to 70 dynes/cm, in order to yield an aerosol having the target aerosol particle diameter. Surface tension of a given formulation may be adjusted by adding a surfactant. In certain embodiments, the solution can have a pH in the range of about 3.0 to 8.5, an osmotic pressure between about 150 mOsm/kg to 880 mOsm/kg, and a NaCl equivalency between about 0.9% NaCl to 3.0% NaCl.

Active ingredients which can be of some use for treating the aforementioned indications include, but are not limited to, substances selected from the group of anti-inflammatory drugs, anti-emetics, glucocorticoids, anti-infective agents, antibiotics, fungicides, virucides either alone or in combination with biofilm-reducing compounds or inhibitors of efflux pumps, antiseptics, immunomodulators, antioxidants, mycolytica, decongestives, vasoconstrictors, non-steroidal anti-inflammatory drugs (NSAIDS), neurological agents, wound-treatment agents, local anesthetics, peptides, proteins and natural or synthetic plant extracts.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
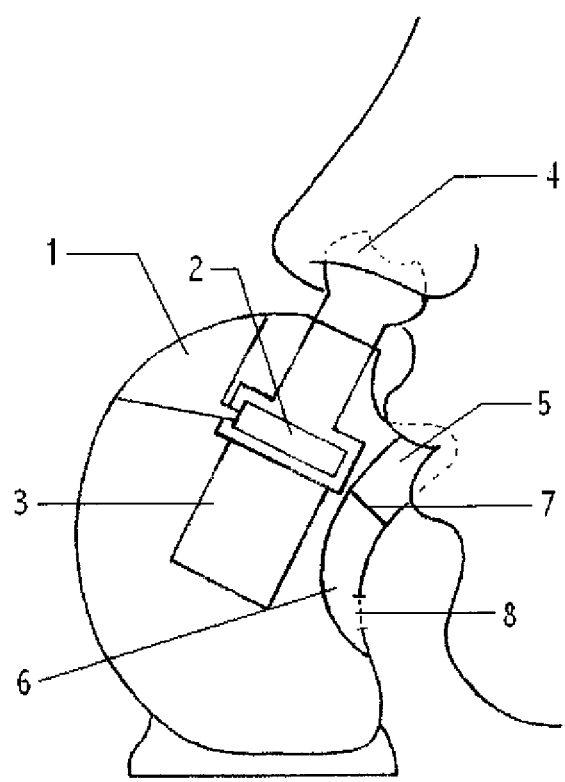
FIG. 1 is a perspective view of one embodiment of the aerosol therapy device described herein. The device comprises an aqueous drug reservoir (1) being connected to an aerosol generator (2) being connected to an air-flow supply device (3) to carry the aerosol particles in a single pulsated airflow through a twin-port nosepiece (4) to direct the single airflow comprising aerosol particles into one of the two alae of the nose wherein the device operates when the user exhales into the exhalation triggering device comprising a pipe/mouthpiece (5), flow detector/sensor (6), flow restrictor (7), and air outlet (8).

The present invention addresses the inadequacies of current sinunasal therapies by providing increased aerosol delivery of an active agent to the paranasal sinuses via the aerosol delivery of the active agent with a pulsating flow of air comprising a pressure field which, acting under the principles described above related to the Helmholtz resonator, results in increased aerosol penetration through the ostia of the sinus and increase aerosol deposition within the paranasal cavity.

In other embodiments, the aerosol therapy device described herein can provide increase aerosol delivery of an active agent to the nasal passages and/or sinuses for the topical delivery of an active agent to a patient in need thereof. In still other embodiments, the aerosol therapy device described herein can provide increase aerosol delivery of an active agent to the nasal passages and/or sinuses for the systemic delivery of an active agent to a patient in need thereof. In yet other embodiments, the aerosol therapy device described herein can provide increase aerosol delivery of an active agent to the olfactory region of the nasal passages for the delivery of an active agent to the central nervous system of a patient in need thereof. In certain aspects, the active agent comprises an active pharmaceutical ingredient. In other aspects, the active agent is a substance or chemical that is generally regarded as safe but does not comprise an active pharmaceutical ingredient.

In certain embodiments, the present invention can comprise an aerosol therapy device for the delivery of an active agent to the paranasal sinuses wherein the aerosol therapy device comprises an aqueous drug reservoir (1), the aqueous drug reservoir being connected to an aerosol generator (2) for the generation of an aerosol particles, the aerosol generator being connected to an air-flow supply device (3), the air-flow supply device producing a single airflow to carry the aerosol particles, wherein the single airflow consists of a pulsating flow of air and comprises an pressure field produced by a pulsed pressure wave, wherein said pulsating airflow pulsates at a frequency greater than 100 Hz and a twin-port nosepiece (4) to direct the single airflow comprising aerosol particles into one of the two alae of the nose, wherein the device delivers the aerosol particles of the active agent to the paranasal sinuses. In certain other embodiments, the device can further comprise an exhalation triggering pipe/mouthpiece (5). In certain aspects, the active agent comprises an active pharmaceutical ingredient. In other aspects, the active agent is a substance or chemical that is generally regarded as safe but does not comprise an active pharmaceutical ingredient.

In certain embodiments, the present invention can be a bench top device. In other embodiments, the present invention can be a portable device, such as a handheld device or handheld device with a pod. In certain embodiments, the device is operated by electricity via batteries or an AC adapter, pneumatic or hydraulic pressure, or a combination thereof.

DEFINITIONS

As used in the present specification, the following words and phrases are generally intended to have the meanings as set forth below, except to the extent that the context in which they are used indicates otherwise.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

The term "about" is used synonymously with the term "approximately." As one of ordinary skill in the art would understand, the exact boundary of "about" will depend on the component of the composition or other parameter. Illustratively, the use of the term "about" with regard to a certain parameter indicates that values slightly outside the cited values, i.e., plus or minus 0.1% to 10%, which are also effective and safe.

As used herein, "active agent" refers to any substance or mixture of substances intended to furnish a direct or indirect effect in the diagnosis, cure, mitigation, treatment, or prevention of disease or to affect the structure and function of the body. In certain embodiments, the active agent can comprise an active pharmaceutical ingredient. In other embodiments, the active agent can comprise a substance or chemical that is generally regarded as safe but is not an active pharmaceutical ingredient.

The term "aerosol" is used synonymously with the term "aerosolized agent," and refers to a composition comprising airborne liquid droplets generated by the aerosolization or vaporization of an aqueous drug or aqueous aerosol mixture.

As used herein, "aqueous drug," "aqueous drug solution," or "aqueous aerosol mixture," refer to any aqueous dosage form for the aerosolized or vaporized delivery of an active or in-active agent. Examples of suitable aqueous drugs include, but are not limited to, solutions, dispersions, emulsions, colloidal liquids, micelle or mixed micelle liquids, liposomal liquids, nanosuspensions, and suspensions.

The term "nasal passage" refers to any areas of the nasal region referred to as the nasal vestibule, palate, inferior turbinate, middle turbinate, superior turbinate, nasopharnyx and olfactory region.

Air Flow Supply Device

In the present invention, an aerosol comprising an active agent is delivered to the nasal cavity by an aerosol therapy device which comprises an air flow supply device that simultaneously and/or concurrently generates high frequency pulses of air which consists of oscillating pressure fields. The pulsated air flow which carries the aerosol may be generated in various forms of actuators (e.g. air flow supply device and/or pump). In certain embodiments, a pulsed pressure wave can be added by modulating the drive signal amplitude of the air flow supply device. In one embodiment, the pulsated air flow is generated by a micro diaphragm pump or a microelectromechanical (MEMS) actuator.

Figure 2:
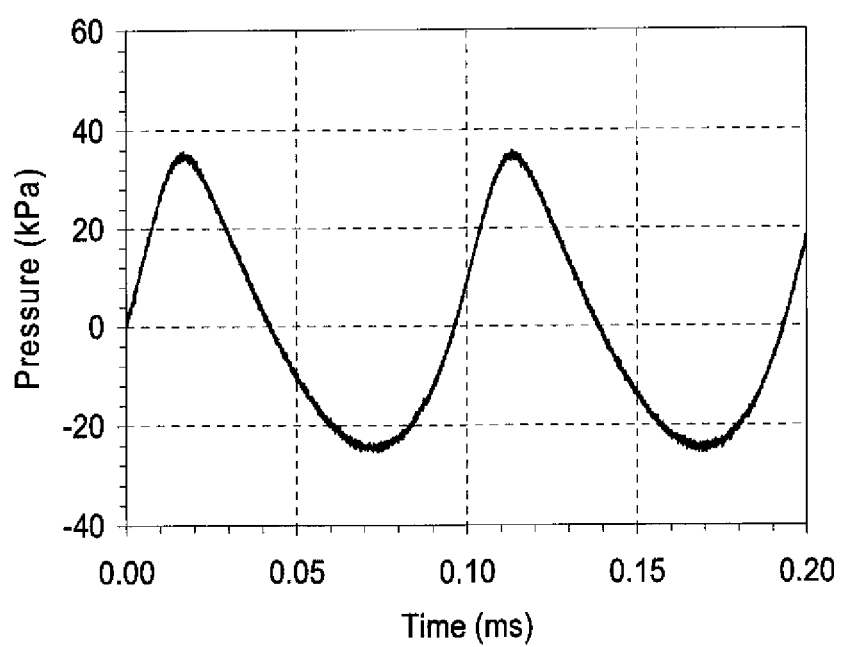
FIG. 2 is a graph of an acoustic pressure signal, measured near to the central anti-node in the cavity of the air flow supply device, showing the non-linear effects on the wave-form.
Figure 3:
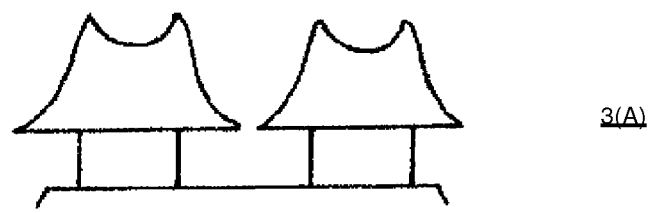
FIGS. 3(A), 3(B) and 3(C) are various views of a twin-port nosepiece wherein the port comprise independent truncated cones.
Figure 3:
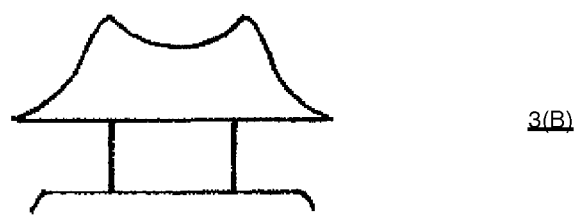
Figure 3:
Figure 4:
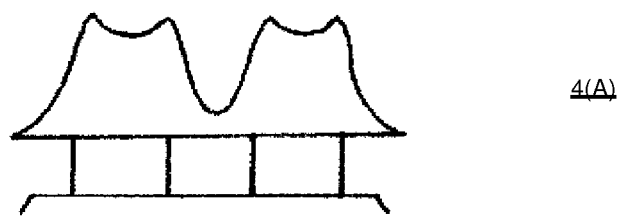
FIGS. 4(A), 4(B) and 4(C) are various views of a twin-port nosepiece wherein the port comprise truncated cones connected at the middle.
Figure 4:
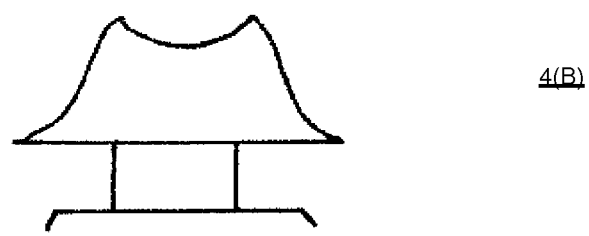
Figure 4:
Figure 5:
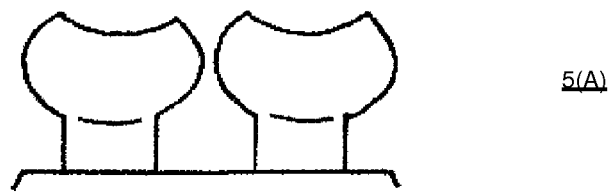
FIGS. 5(A), 5(B) and 5(C) are various views of a twin-port nosepiece wherein the port comprise independent bulb shaped ports.
Figure 5:
Figure 5:
Figure 6:
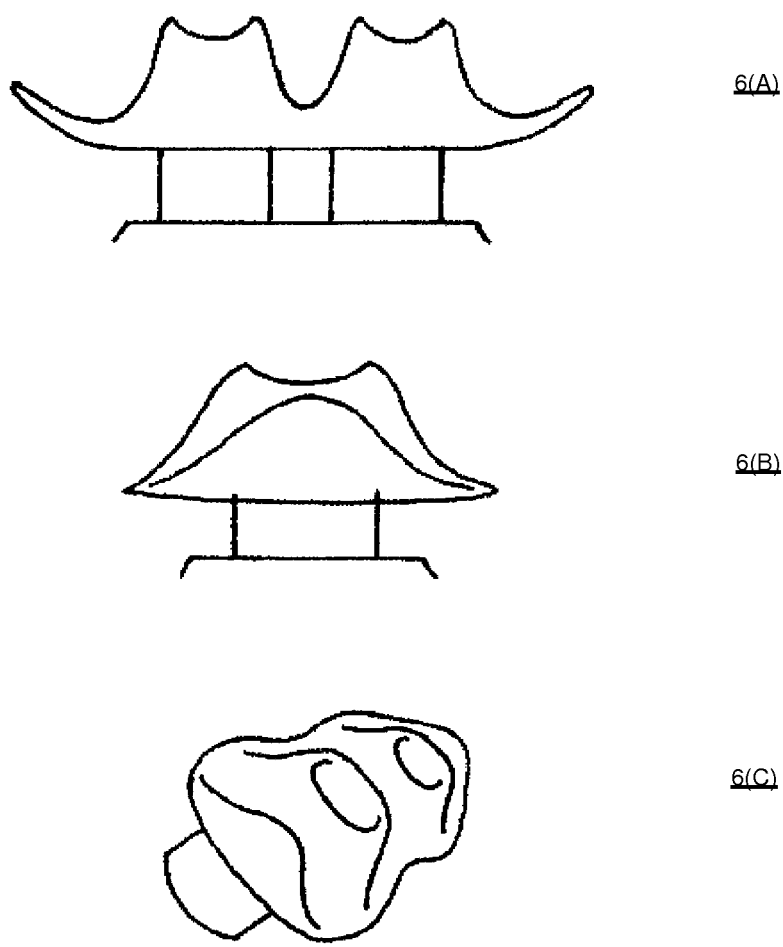
FIGS. 6(A), 6(B) and 6(C) are various views of a twin-port nosepiece wherein the port comprise truncated cones connected at the middle, further comprising protruding side shields for a better fit and tighter seal.
Figure 7:
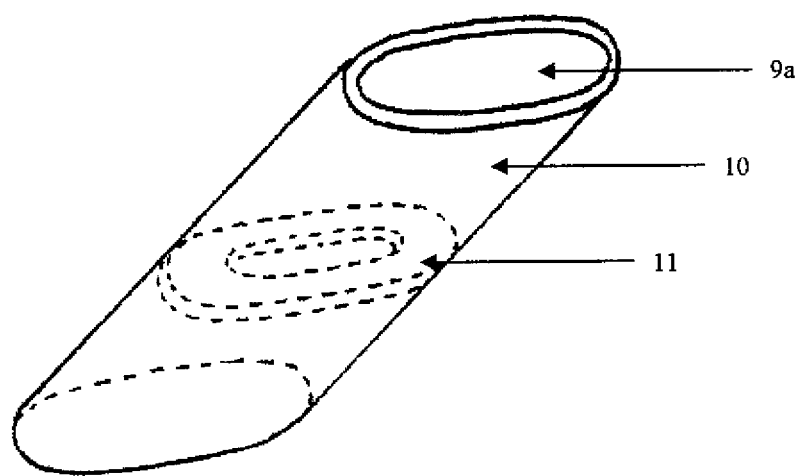
FIG. 7 is a perspective view of an exhalation mouthpiece comprising a distal opening (9a) for the patient to breath into, a cavity for a one way valve (10), and a restrictor (11) to control the air flow.
Figure 8:
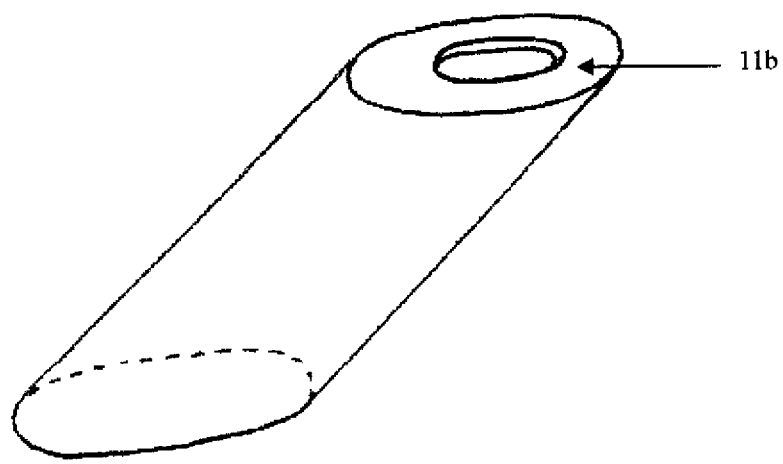
FIG. 8 is a perspective view of an exhalation mouthpiece wherein a restrictor (11b) is located on the distal end.
Figure 9:
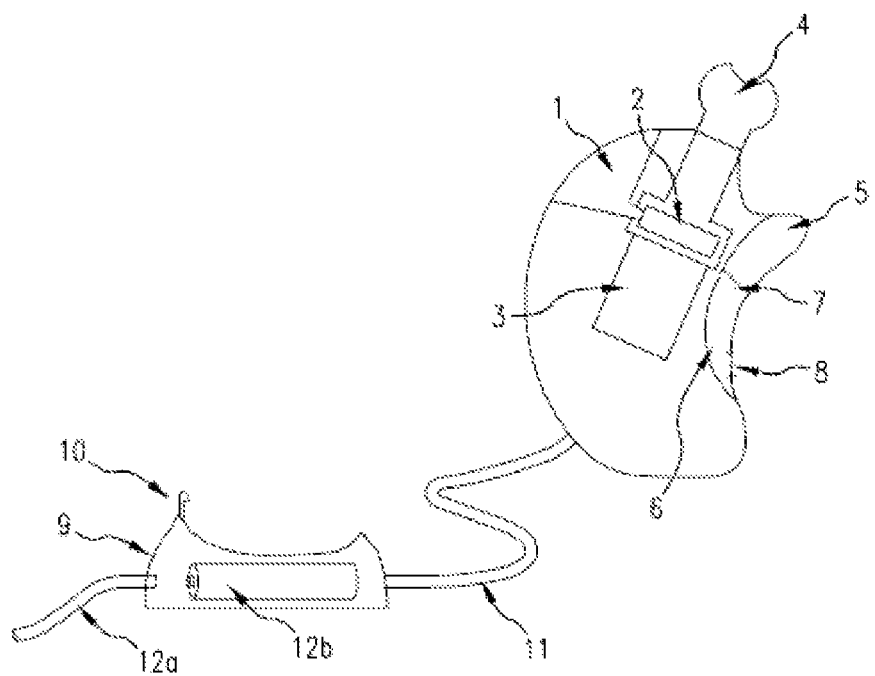
FIG. 9 is a perspective view of one embodiment of the aerosol therapy device described herein. The device comprises an aqueous drug reservoir (1) being connected to an aerosol generator (2) being connected to an air-flow supply device (3) to carry the aerosol particles in a single pulsated airflow through a twin-port nosepiece (4) to direct the single airflow comprising aerosol particles into one of the two alae of the nose wherein the device operates when the user exhales into the exhalation triggering device comprising a pipe/mouthpiece (5), flow detector/sensor (6), flow restrictor (7), and air outlet (8). In this embodiment, the aerosol delivery device further comprises a bench top base (9) comprising a latch (10), thereby allowing for removal of the device from the base, a tether cord (11), a connector cord to a power source (12a), and rechargeable batteries (12b).

In certain embodiments, the air flow supply device or pump can be driven by a piezoelectric or piezoceramic element, for example a crystal in a shape of a disk. In this embodiment, the piezoelectric disk produces a mechanical deformation when an electric potential is applied. The deformation drives a resonant acoustic cavity adjacent to the piezoelectric disk to generate a pressure field confined within the air flow supply device. The pressure field has regions of high pressure fluctuations (antinodes) and other regions of relatively small pressure fluctuations (nodes). In one embodiment, a periodic acoustic wave is used to create a cavity pressure wave that is non-linear at high amplitude as shown in FIG. 2. This can be characterized by a deviation of the pressure wave towards the vacuum limit, and a corresponding sharpening of the positive excursion, thereby increasing the typical positive pressure to over 100 kPa (1 Bar). In yet other embodiments, various other forms of pressure waves can be produced, such as a sine wave, square wave, triangle wave, sawtooth wave, pulse wave, and other symmetric or non-symmetric waveforms.

As described herein, the pulsed flow of air from the air flow supply device and/or pump is used to carry the aerosol into the patient's nasal cavity within a defined oscillating pressure field. The same pumping function to create the pressure field can be used to generate a convective flow through an air outlet, thereby delivering a pulsated airflow to carry the aerosol to the nasal cavity. In certain embodiments, inlet and/or outlet check valves operable at high frequencies can be used to prevent back flow and create the positive air flow. In certain embodiment, a passive check valve can be used, such as "duck-bill" type valves. In other embodiments, the check valve can be a ball valve, flapper valve or nozzle-flapper valve. In yet other embodiments, other means for providing substantially passive valving function can be used, such as a plunger, shuttle, rotary stop-cock, flap, or one-way flow gate. In other embodiments, the air flow supply device is valveless. In one embodiment, a diffuse/nozzle is used create the positive air flow. In another embodiment, an unsymmetrical corrugation chamber bottom (UCCB) is used to create the positive air flow. In still other embodiments, a solenoid is used to control the fluid flow. In yet other embodiments, an air outlet is in the center of the pump cavity and multiple air inlets are positioned around the piezoelectric disc to obtain an adequate air supply for positive flow without the use of a check valve.

In other embodiments, the air flow supply device or pump can be driven by a shape memory alloy. In one embodiment the shape memory alloy can be a nickel-titanium alloy that has the ability to return to a previously defined shape when subjected to a thermal potential. The shape memory alloy can be configured in a coil and operated as a spring, triggered by thermal energy.

In yet other embodiments, a thermopneumatic pump can be used. In this embodiment, a thin-film resistive heater is put inside an air cavity with a diaphragm membrane. The heater can be heated to deform the diaphragm thus creating a pulsated air flow.

In still other embodiments, the air flow supply device or pump can be driven by a magnetostrictive disk. In certain embodiments the magnetostrictive material can be a cobalt, cobalt alloy, or Terfenol-D. In this embodiment, the magnetostrictive air flow supply device or pump produces a mechanical deformation when a magnetic field is applied.

In other embodiments, the air flow supply device or pump can be an electromagnetic system. In this embodiment, a valve cap is made of a soft magnetic material, such as Ni—Fe, and is normally in the close position with a compression spring. A magnetic field is applied, in one embodiment by a solenoid coil, moving the valve cap into the open position.

In yet other embodiments, the air flow supply device or pump can be an electrostatic system. In this embodiment, a movable and fixed electrode is used. The electrostatic driver is used to pulse the diaphragm membrane.

In still other embodiments, the air flow supply device or pump can be a bimetallic system. In this embodiment, a circular diaphragm made of bimetallic material is equipped with a circular heater. The heater changes the temperature of the bimetal and triggers the displacement of the diaphragm.

In yet other embodiments, the air flow supply device or pump can be driven by an electro-active polymer (EAP) disk. In this embodiment, the EAP pump produces a mechanical deformation when a voltage is applied. In one embodiment the polymer can be a dielectric EAP. In another embodiment the polymer can be an ionic EAP.

In yet still other embodiments, a mechanically driven diaphragm pump creates a pulsated air flow comprising an oscillating pressure field. In one embodiment, the pressure fluctuation is generated by a piston rod attached to a diaphragm membrane, which seals a hollow space (pressure chamber) which will generate the acoustic sound field. In this embodiment, the piston rod can be supported eccentrically on a driving pulley so that the piston rod causes a pressure-fluctuation-generating movement of the membrane when the driving pulley turns. In this embodiment, the driving pulley can be connected to an electric motor or another suitable drive. The pulsating frequency can be adjusted by altering the electrical input into the motor and/or adjusting the pulley gears.

In other embodiments, a mechanically driven diaphragm pump can be operated by a pneumatic cylinder. In this embodiment, the pneumatic cylinder can have an associated shaft that is attached to a membrane with a hollow space to create the pulsated air flow. In other embodiments, an electronic control circuit can be used to operate a solenoid, which in turn controls the frequency at which the pneumatic cylinder is operated. In one embodiment the solenoid can be a nozzle-flapper type servo valve. In another embodiment, the cylinder can be a hydraulic cylinder fed by hydraulic fluid under the control of a servo valve and hydraulic pump.

In still other embodiments, a pneumatic pump can be used without a mechanical shaft. In one embodiment, the pneumatic drive directly creates the pressure-fluctuation, generating movement of the diaphragm membrane or a piston. The pressure chamber on the adjacent side of the membrane can create the acoustic sound field with an inlet and outlet creating the positive flow. In yet other embodiments, a hydraulic drive can directly create the diaphragm membrane movement by hydraulic fluid.

In other embodiments, a turbine can be used to generate the pulsated air flow comprising an oscillating pressure field. In certain other embodiments, the turbine can be used in conjunction with the pneumatic and hydraulic pumps described above.

In yet still other embodiments, a peristaltic pump such as a roller or centrifugal pumps can be used to obtain the pulsated air flow. In other embodiments, a single piston pump or a rapid refill pump can be used. In certain other embodiments, a rotary pump or a rotary piston pump can be used. In one embodiment, an offset drive is used to create simultaneous rotary and linear motion on the piston resulting in an intake and discharge cycle. The stroke length of the piston and rate the piston travels is adjusted to achieve the desired frequency and air pressure. In another embodiment, a linear actuator is used to drive a single two-piece pump module. The actuator can either drive the piston in a linear motion for displacement or in a rotary motion to accomplish valving. The sequencing of the displacement and valving creates a high frequency pulsated air flow.

In still other embodiments, the pulsated air flow can be generated by spinning a disc comprising different cut openings. In this embodiment, altering the size of the cut openings, the location or orientation of the cut openings, the quantity of cut openings, and/or rpm of the controlled motor one can control the pulse frequency and/or pressure of the air flow.

In certain embodiments, the air flow supply device provides a pulsated flow of air having a pulse frequency of greater than 100 Hz. In certain other embodiments the pulse frequency can comprise the ultrasonic range from about 150 Hz to about 20 KHz. In still other embodiments, the pulse frequency can be from about 200 Hz to about 20 KHz. In one embodiment, the airflow pulsates at a frequency from about 300 Hz to about 10 KHz. In certain other embodiments, the pulse frequency can be selected to achieve the Helmholtz resonator frequency of the average human adult sinuses (both pre and/or post-surgical), which typically ranges from about 150 to about 6000 Hz (see, e.g., Table 1). In yet other embodiments, the pulse frequency can be selected to achieve the Helmholtz resonator frequency for the sinuses of an average human child between the ages of 5 year and 15 years old, which typically ranges from about 200 to about 2500 Hz (see, e.g., Table 2). In other embodiments, the pulse frequency can be adjusted to the typical Helmholtz resonator frequency of a particular sinus (e.g., maxillary, sphenoid, ethmoid, or frontal), thereby achieving selective aerosol delivery to a particular sinus. By way of a non-limiting example, the pulse frequency can be adjusted to the typical Helmholtz resonator frequency of the average maxillary sinus, thereby achieving selective aerosol delivery to the maxillary sinuses in a particular patient. In another embodiment, the pulse frequency can be adjusted to the typical Helmholtz resonator frequency of the average sphenoid sinus, thereby achieving selective aerosol delivery to the sphenoid sinuses in a particular patient. In still another embodiment, the pulse frequency can be adjusted to the typical Helmholtz resonator frequency of the average ethmoid sinus, thereby achieving selective aerosol delivery to the ethmoid sinuses in a particular patient. In yet still another embodiment, the pulse frequency can be adjusted to the typical Helmholtz resonator frequency of the average frontal sinus, thereby achieving selective aerosol delivery to the frontal sinuses in a particular patient The Helmholtz resonator causes an oscillation of the air within the neck of the resonator, at a frequency given by equation (1). Using the typical values of the parameters in equation (1), the resonant frequency of typical adult sinuses (e.g., (i) pre-surgical (ostia diameter of 1.5 mm); (ii) post-surgical (ostia diameter of 3.0 mm to 3.5 mm) are shown in Table 1 and the resonant frequency of typical children sinuses (child age 5; child age 10; and child age 15) are shown in Table 2.

$$f_H = \frac{c}{2\pi}\sqrt{\frac{A}{V_0 L}} \quad (1)$$

TABLE 1

Exemplary Helmholtz frequency for the Adult paranasal sinus cavities (pre and/or post surgery)

|  | Speed of Sound in Air - (cm/s) (c) | 2 × pi | Diameter Cavity Opening (mm) | Area of Cavity Opening (cm 2) (A) | Volume of Sinus Cavity (cm3) (V) | Length of Neck (mm) (L) | Freq. Hz |
|---|---|---|---|---|---|---|---|
| Post Surgical | | | | | | | |
| Maxillary | 343000 | 6.28 | 10.0 | 0.00785 | 7.5 | 2.0 | 3,950 |
| Sphenoid | 343000 | 6.28 | 10.0 | 0.00785 | 8.2 | 2.0 | 3,778 |
| Ethmoid | 343000 | 6.28 | 10.0 | 0.00785 | 14.0 | 2.0 | 2,891 |
| Frontal | 343000 | 6.28 | 10.0 | 0.00785 | 10.0 | 2.0 | 3,421 |
| Post Surgical | | | | | | | |
| Maxillary | 343000 | 6.28 | 3.5 | 0.00096 | 14.7 | 2.0 | 987 |
| Sphenoid | 343000 | 6.28 | 3.5 | 0.00096 | 8.2 | 2.0 | 1,322 |
| Ethmoid | 343000 | 6.28 | 3.5 | 0.00096 | 14.0 | 2.0 | 1,012 |
| Frontal | 343000 | 6.28 | 3.5 | 0.00096 | 10.0 | 2.0 | 1,197 |
| Pre Surgical | | | | | | | |
| Maxillary | 343000 | 6.28 | 1.5 | 0.00018 | 6.8 | 2.0 | 625 |
| Sphenoid | 343000 | 6.28 | 1.5 | 0.00018 | 7.4 | 2.0 | 597 |
| Ethmoid | 343000 | 6.28 | 1.5 | 0.00018 | 12.6 | 2.0 | 457 |
| Frontal | 343000 | 6.28 | 1.5 | 0.00018 | 9.0 | 2.0 | 541 |
| Post Surgical | | | | | | | |
| Maxillary | 343000 | 6.28 | 10.0 | 0.00785 | 7.5 | 1.0 | 5,586 |
| Sphenoid | 343000 | 6.28 | 10.0 | 0.00785 | 8.2 | 1.0 | 5,343 |
| Ethmoid | 343000 | 6.28 | 10.0 | 0.00785 | 14.0 | 1.0 | 4,089 |
| Frontal | 343000 | 6.28 | 10.0 | 0.00785 | 10.0 | 1.0 | 4,838 |

TABLE 1-continued

Exemplary Helmholtz frequency for the Adult paranasal sinus cavities (pre and/or post surgery)

|  | Speed of Sound in Air - (cm/s) (c) | 2 × pi | Diameter Cavity Opening (mm) | Area of Cavity Opening (cm 2) (A) | Volume of Sinus Cavity (cm3) (V) | Length of Neck (mm) (L) | Freq. Hz |
|---|---|---|---|---|---|---|---|
| Post Surgical | | | | | | | |
| Maxillary | 343000 | 6.28 | 3.5 | 0.00096 | 14.7 | 1.0 | 1,396 |
| Sphenoid | 343000 | 6.28 | 3.5 | 0.00096 | 8.2 | 1.0 | 1,870 |
| Ethmoid | 343000 | 6.28 | 3.5 | 0.00096 | 14.0 | 1.0 | 1,431 |
| Frontal | 343000 | 6.28 | 3.5 | 0.00096 | 10.0 | 1.0 | 1,693 |
| Pre Surgical | | | | | | | |
| Maxillary | 343000 | 6.28 | 1.5 | 0.00018 | 6.8 | 1.0 | 883 |
| Sphenoid | 343000 | 6.28 | 1.5 | 0.00018 | 7.4 | 1.0 | 845 |
| Ethmoid | 343000 | 6.28 | 1.5 | 0.00018 | 12.6 | 1.0 | 646 |
| Frontal | 343000 | 6.28 | 1.5 | 0.00018 | 9.0 | 1.0 | 765 |
| Post Surgical | | | | | | | |
| Maxillary | 343000 | 6.28 | 10.0 | 0.00785 | 7.5 | 3.0 | 3,225 |
| Sphenoid | 343000 | 6.28 | 10.0 | 0.00785 | 8.2 | 3.0 | 3,085 |
| Ethmoid | 343000 | 6.28 | 10.0 | 0.00785 | 14.0 | 3.0 | 2,361 |
| Frontal | 343000 | 6.28 | 10.0 | 0.00785 | 10.0 | 3.0 | 2,793 |
| Post Surgical | | | | | | | |
| Maxillary | 343000 | 6.28 | 3.5 | 0.00096 | 14.7 | 3.0 | 806 |
| Sphenoid | 343000 | 6.28 | 3.5 | 0.00096 | 8.2 | 3.0 | 1,080 |
| Ethmoid | 343000 | 6.28 | 3.5 | 0.00096 | 14.0 | 3.0 | 826 |
| Frontal | 343000 | 6.28 | 3.5 | 0.00096 | 10.0 | 3.0 | 978 |
| Pre Surgical | | | | | | | |
| Maxillary | 343000 | 6.28 | 1.5 | 0.00018 | 6.8 | 3.0 | 510 |
| Sphenoid | 343000 | 6.28 | 1.5 | 0.00018 | 7.4 | 3.0 | 488 |
| Ethmoid | 343000 | 6.28 | 1.5 | 0.00018 | 12.6 | 3.0 | 373 |
| Frontal | 343000 | 6.28 | 1.5 | 0.00018 | 9.0 | 3.0 | 442 |

TABLE 2

Exemplary Helmholtz frequency for the child paranasal sinus cavities (child age 5, child age 10, and child age 15)

|  | Speed of Sound in Air - (cm/s) (c) | 2 × pi | Diameter Cavity Opening (mm) | Area of Cavity Opening (cm 2) (A) | Volume of Sinus Cavity (cm3) (V) | Length of Neck (mm) (L) | Freq. Hz |
|---|---|---|---|---|---|---|---|
| Child - age 5 | | | | | | | |
| Maxillary | 343000 | 6.28 | 1.5 | 0.00018 | 4.0 | 1.0 | 1,147 |
| Sphenoid | 343000 | 6.28 | 1.5 | 0.00018 | 0.5 | 1.0 | 3,245 |
| Child - age 10 | | | | | | | |
| Maxillary | 343000 | 6.28 | 1.5 | 0.00018 | 10.0 | 1.0 | 726 |
| Sphenoid | 343000 | 6.28 | 1.5 | 0.00018 | 1.3 | 1.0 | 2,013 |
| Child - age 15 | | | | | | | |
| Maxillary | 343000 | 6.28 | 1.5 | 0.00018 | 16.0 | 1.0 | 574 |
| Sphenoid | 343000 | 6.28 | 1.5 | 0.00018 | 2.5 | 1.0 | 1,451 |
| Child - age 5 | | | | | | | |
| Maxillary | 343000 | 6.28 | 1.0 | 0.00008 | 4.0 | 2.0 | 541 |
| Sphenoid | 343000 | 6.28 | 1.0 | 0.00008 | 0.5 | 2.0 | 1,530 |
| Child - age 10 | | | | | | | |
| Maxillary | 343000 | 6.28 | 1.0 | 0.00008 | 10.0 | 2.0 | 342 |
| Sphenoid | 343000 | 6.28 | 1.0 | 0.00008 | 1.3 | 2.0 | 949 |
| Child - age 15 | | | | | | | |
| Maxillary | 343000 | 6.28 | 1.0 | 0.00008 | 16.0 | 2.0 | 270 |
| Sphenoid | 343000 | 6.28 | 1.0 | 0.00008 | 2.5 | 2.0 | 684 |
| Child - age 5 | | | | | | | |
| Maxillary | 343000 | 6.28 | 1.5 | 0.00018 | 4.0 | 2.0 | 811 |
| Sphenoid | 343000 | 6.28 | 1.5 | 0.00018 | 0.5 | 2.0 | 2,295 |

TABLE 2-continued

Exemplary Helmholtz frequency for the child paranasal sinus cavities (child age 5, child age 10, and child age 15)

| | Speed of Sound in Air - (cm/s) (c) | 2 × pi | Diameter Cavity Opening (mm) | Area of Cavity Opening (cm2) (A) | Volume of Sinus Cavity (cm3) (V) | Length of Neck (mm) (L) | Freq. Hz |
|---|---|---|---|---|---|---|---|
| Child - age 10 | | | | | | | |
| Maxillary | 343000 | 6.28 | 1.5 | 0.00018 | 10.0 | 2.0 | 513 |
| Sphenoid | 343000 | 6.28 | 1.5 | 0.00018 | 1.3 | 2.0 | 1,423 |
| Child - age 15 | | | | | | | |
| Maxillary | 343000 | 6.28 | 1.5 | 0.00018 | 16.0 | 2.0 | 406 |
| Sphenoid | 343000 | 6.28 | 1.5 | 0.00018 | 2.5 | 2.0 | 1,026 |

In certain embodiments, the air flow supply device provides a pulsated flow of air to achieve optimum deposition of the active agent to the CNS through the olfactory route. In certain embodiments, the range of useful frequencies can be from about 1 Hz to about 20 KHz. In other embodiments, the frequency can be from about 1 Hz to about 10 KHz. In yet other embodiments, the frequency can be from about 100 Hz to about 1 KHz. In yet still other embodiments, the frequency can be from about 300 Hz and about 700 kHz. In still yet other embodiments, the frequency can be about 500 Hz. In other embodiments, the frequency can be from about 10 Hz to about 100 Hz.

Various means of altering the frequency is known to one skilled in the art, for example, by speeding up or speeding down the pumping action of the air flow supply device. In other embodiments, the temperature of the piezoelectric crystal can be altered to change the frequency.

In certain embodiments, the pressure wave can be based on a square wave. In other embodiments, the pressure wave can be modified with a profile function to sharpen or smooth the changing pressure gradients.

In other embodiments, the pressure field can be produced by a conventional audio amplifier and speaker set. In still other embodiments, the conventional audio amplifier and speaker set is used in conjunction with the pulsated flow from the air flow supply device described. In certain embodiments, the pressure field is an acoustic pressure field.

In yet other embodiments, the device can have self-tuning capabilities. Self-tuning to the resonant frequency can be achieved by circuitry comprising transformers and oscillator transistors known to one skilled in the art. In certain embodiments, a microphone is attached within the nosepiece such that the microphone is positioned near or inside the patient's nasal cavity to measure the frequency for self-tuning. Microphones suitable for use include, but are not limited to, solid state microphones, dynamic microphones, ribbon microphones, carbon microphones, piezoelectric microphones, laser microphones, or digital microphones such as a silicone chip microphone. In other embodiments, a self-tuning drive circuitry is provided wherein the actuator comprises a feedback electrode which provides a feedback signal to the drive circuit. In yet other embodiments, laser imaging techniques can be used for self-tuning.

In still other embodiments, the pulse frequency can be swept across the typical optimum frequency range of each of the four paranasal sinuses during patient use by real time adjustment of the air flow supply device speed, thereby providing targeted delivery of the aerosol to each of the paranasal sinuses. In certain embodiments, the Helmholtz frequency of a person can be determined before treatment and the range of frequencies would be centered at this frequency. In one embodiment, the pulse frequency is swept across the frequency range of about 150 Hz to about 6000 Hz. In another embodiment, the pulse frequency is swept across the frequency range of about 200 Hz to about 5000 Hz. In yet another embodiment, the pulse frequency is swept across the frequency range of about 300 Hz to about 4000 Hz. In still yet another embodiment, the pulse frequency is swept across the frequency range of about 500 Hz to about 3000 Hz. In yet still another embodiment, the pulse frequency is swept across the frequency range of about 150 Hz to about 2500 Hz.

In still other embodiments, the sweeping function is used in conjunction with the self-tuning function. In this embodiment, the device can first self-tune to find the optimum frequency to achieve increased sinus deposition. Then the device can sweep a range of frequencies of which the ascertained optimum frequency will be the mid point of the range.

The pressure of the air flow is adjusted to reach optimum sinus deposition. With the use of higher frequencies, the delivery pressure can be reduced without significant loss in sinus deposition. In certain embodiments, the pressure can be about 5 to about 50 mbar. In other embodiments, the pressure can be about 15 to about 40 mbar. In yet other embodiments, the pressure can be about 15 to about 25 mbar. Even higher amplitudes than about 50 mbar can be useful for certain patients and indications in which some degree of discomfort to the patients may be found acceptable, such as serious diseases and affections of the sinus mucosa. In another embodiment, a safety valve is equipped to prevent overpressure of the nasal cavity.

In certain embodiments, the air flow supply device further comprises a heating element to control the temperature of the air being delivered to the patient.

Nosepiece

In the present invention, the aerosol is delivered to the nasal cavity by an aerosol therapy device which comprises a nosepiece to direct the single airflow comprising aerosol particles into one of the two alae of the nose or to both alae of the nose. In certain embodiments, the nosepiece can be made of any suitable material such as a metal or metal alloy, plastics, rubber, silicone, urethane, other suitable polymers, and combinations thereof. In certain embodiments, the nosepiece is permanently attached to the device. In certain other embodiments, the nosepiece is removable and replaceable. In still other embodiments, the nosepiece is a twin-port nosepiece.

The nosepiece can be shaped to obtain an air tight seal at the Mae of the nose. In certain embodiments, the ends to be inserted into the alae can take the shape of independent truncated cones with an aperture angle in a range of 10° to 80°. In other embodiments, the aperture angle can be in a range of 20° to 60°. In yet other embodiments, the aperture angle can be in a range of 30° to 40°. In yet still other embodiments, the aperture angle can be in a range of 40° to 70°. In other embodiments, the ends to be inserted can take the shape of a bulb.

In certain embodiments, the ends to be inserted can be connected with a centerpiece. In other embodiments, side shields can be provided for better fit and tighter seal. In certain other embodiments, the ends to be inserted into the alae can comprise an inflatable balloon device in an annular shape whereby the balloon device has a cross section emulating a truncating cone when inflated. Said inflatable balloon device can be operated via a compressed air supply, for example with the compressed air supply for the aerosol generator, via a throttle, or with a manually operated pump.

In certain embodiments, the nosepiece can be shaped such that the air tight seal is obtained while achieving easy oral access to an attached mouthpiece. In certain embodiments, the nosepiece can be inclined such that when the device is held vertically, the nosepiece can be placed simply and comfortably in the patient's alae. In other embodiments, one or more flex joints can be used to obtain the tight air seal and comfortable mouth piece access.

In certain embodiments, the aerosol can be delivered to both alae of the nose simultaneously by a twin-port nosepiece. In certain embodiments, the aerosol can be delivered to one of the two alae by a twin-port nosepiece. In other embodiments, the nosepiece comprises a flow resistance means via a stopper for one ala, thereby delivering aerosol to only one of the two alae. In one embodiment, the stopper comprises a hollow cavity, a hole connecting said hollow cavity with the nasal cavities of the patient, a smaller second hole located on the stopper to achieve optimum back pressure. In still other embodiments, the aerosol flow can be alternated between the alae, delivering the aerosol to one of the two alae at a time. In certain embodiments, the flow to each ala is carried out in intervals ranging from 1 second intervals to two minute intervals. In one embodiment, the flow to each ala is carried out in 1 second intervals (e.g., for the intranasal delivery of a vaccine). In another embodiment, the flow to each ala is carried out in 5 second intervals. In yet another embodiment, the flow to each ala is carried out in 10 second intervals. In another embodiment, the flow to each ala is carried out in 15 second intervals. In still another embodiment, the flow to each ala is carried out in 30 second intervals. In yet another embodiment, the flow to each ala is carried out in 45 second intervals. In still yet another embodiment, the flow to each ala is carried out in 1 minute intervals. In yet still another embodiment, the flow to each ala is carried out in two minute intervals Various means for altering the flow direction and/or creating back pressure can be recognized by one skilled in the art. In certain embodiment, the alternating means can be provided by a mechanical valve, such as a ball or rotor valve. In another embodiment, the mechanical valve comprises a switch or shutter that the user can manually adjust during use. In certain embodiments, the mechanical valve can be controlled by an actuator such as an electric motor. In other embodiments, an electromechanical valve can be used, such as a solenoid. In other embodiments, a diaphragm valve can be used. In still other embodiments, pneumatic actuators or hydraulic actuators can be used. In certain embodiments, back pressure can be created by having a small opening on the otherwise sealing portion of the nosepiece, thus instead of completely sealing the flow to one ala, the flow is only restricted, creating back pressure to the aerosol flowing into the other ala. In one embodiment, the small opening is created by not fully closing the alternating means, such as a valve. In another embodiment, the small opening is a separate opening such as a hole on the sealing lid of the alternating means, thus allowing air to flow through the hole when the valve is in the sealed position. In yet other embodiments, a microprocessor can be used in conjunction to alter the parameters such as the delivery time interval.

Aerosol Generator

As described herein, the aerosol can be generated by any aerosol or vapor generating device known in the art, e.g., a pneumatic or jet nebulizer-type device or a thermal vaporizer. In certain embodiments, the aerosol generator is selected from the group consisting of a pulsating membrane device, a device comprising a vibrating mesh or plate with multiple apertures, or a device comprising a vibration generator. In certain other embodiments, compressed gas can be used to disperse a liquid into a fine mist.

In certain embodiments, the aerosol can be generated by an ultrasonic device wherein a perforate membrane is vibrated at high frequencies against a body of fluid. In certain embodiments, the vibration is provided by a piezoelectric actuator activated by an electronic drive circuit. In other embodiments, the vibration is provided by magnetostrictive actuation, microelectromechanical actuation, electromagnetic actuation, electric field actuation such as capacitive actuators, or Coulombic actuation.

In one embodiment, the perforate membrane used to generate the aerosol can be a mesh with numerous tapered holes. In certain embodiments, the perforate membrane is a thin plate with many laser-drilled holes as the nozzles. In certain other embodiments, the perforate membrane further comprises geometry to achieve a plume angle such that the aerosol flows to the nosepiece with minimal obstruction. In other embodiments, the perforate membrane is ceramic (including zirconate PZT), steel, gold, silver, copper, zinc, aluminum, or any other combination thereof. In certain other embodiments, the perforate membrane is stainless steel.

In certain other embodiments, the aerosol can be generated by a thermal vaporizer which heats the fluid into aerosols for delivery. In one embodiment, the vaporizer comprises a heating element such as a metal or metal alloy plate or wire coil. In another embodiment, the vaporizer further comprises a secondary heating element to heat the surrounding air and/or heat the air flow for delivery.

As describe herein, the droplet diameter of the aerosols produced by the aerosol generator can be tailored to a particular application. In the embodiment comprising an ultrasonic aerosol generator, the droplet diameter can be controlled by altering the diameter of the laser-drilled holes. In certain embodiments described herein, the holes have a taper. In the embodiment comprising a thermal aerosol generator, the temperature at which the evaporation occurs and/or the temperature of the carrier air flow can be controlled to obtain various droplet diameters with relatively uniform particle size. In other embodiments, the aerosol particles produced by the aerosol generator can have a mass median aerodynamic diameter (MMAD) of about 0.5 µm to about 10 µm. In certain other embodiments, the aerosol particles produced by the aerosol generator can have a MMAD of about 0.5 µm to about 150 µm. In certain other embodiments, the aerosol particles produced by the aerosol generator can have a MMAD of about 2 µm to about 8 µm. In still other embodiments, the aerosol particles produced by the aerosol generator can have a MMAD of about 3 µm to about 5 µm. In still other embodiments, the aerosol particles produced by the aerosol generator can have a MMAD of about 3 µm to about 10 µm. In still other embodiments, the aerosol particles produced by the aerosol generator can have a MMAD of about 1 µm to about 5 µm. In still other embodiments, the aerosol particles produced by the aerosol generator can have a MMAD of about 1 µm to about 30 µm. In still other embodiments, the aerosol particles produced by the aerosol generator can have a MMAD of about 1 µm to about 20 µm. In still other embodiments, the aerosol particles produced by the aerosol generator can have a MMAD of about 1 µm to about 15 µm. In still other embodiments, the aerosol particles produced by the aerosol generator can have a MMAD of about 1 µm to about 10 µm. In still other embodiments, the aerosol particles produced by the aerosol generator can have a MMAD of about 10 µm to about 30 µm. In still other embodiments, the aerosol particles produced by the aerosol generator can have a MMAD of about 10 µm to about 20 µm. In yet other embodiments, the aerosol particles produced by the aerosol generator can have a MMAD of about 5 µm to about 20 µm. In yet still other embodiments, the aerosol particles produced by the aerosol generator can have a MMAD of about 20 µm to about 150 µm. In still other embodiments, the aerosol particles produced by the aerosol generator can have a MMAD of about 20 µm to about 50 µm. In other embodiments, the aerosol particles produced by the aerosol generator can have a MMAD of about 50 µm to about 150 µm.

Aqueous Drug Reservoir

As described herein, the aerosol therapy device comprises a drug reservoir into which the aqueous drug is placed into prior to aerosolization. The drug reservoir is connected to the aerosol generator such that the aqueous drug to be delivered via the aerosol therapy device is fed to the aerosol generator and accelerated through the nozzles to create droplets. In certain embodiments, the reservoir is removable and/or replaceable.

In certain embodiments, the aqueous drug can be directly poured into a reservoir adjacent to the aerosol generator. In other embodiments, the aqueous drug can be provided in a disposable containers filled with individual doses. In this embodiment, the user will place the single dose container, such as an ampoule or vial, directly into a mated fitting of the reservoir, such as a luer or screw fitting. In another embodiment, the drug can be provided to the user as a syringe. In still another embodiment, the reservoir can have an aspirator that aspirates the aqueous drug out of the container into the reservoir. In certain embodiments, the device fits only a certain type of container, thereby dedicating the device to a particular type of aqueous drug. In certain other embodiments, a lock and key function is provided wherein the disposable container provides the delivery device information such as the drug type and optimal delivery parameters for the particular drug and indication of use. In one embodiment, the lock and key function comprises radio frequency identification (RFID) wherein a RFID tag is attached to the ampoule, which provides the delivery device microprocessor the drug and delivery parameter information. In another embodiment, the communication means is provided by an encrypted microchip, which electrically connects to the device when docked into the reservoir.

In certain other embodiments, the aerosol generator forms a part of the wall of the liquid storage container so that an aqueous drug within the liquid storage container directly contacts the aerosol generator, thereby ensuring continuous aerosol generation. In certain embodiments, the aqueous drug in the reservoir is driven to the diaphragm by gravity. In certain other embodiments, a tube is used to drive the aqueous drug to the diaphragm by capillary action.

In certain embodiments, a positive pressure can be applied to the drug reservoir to facilitate delivery of the aqueous drug to the aerosol generator. In one embodiment, the positive pressure can be provided by compressed gas. In another embodiment, the plunger of a syringe can be used to achieve the positive pressure. In other embodiments, venting can be used to obtain the proper flow for the aqueous drug to reach the aerosol generator by gravity.

In certain embodiments, the aerosol therapy device comprises a drug reservoir which can accommodate an aqueous solution having a volume of about 10 mL or less. In one embodiment, the drug reservoir can accommodate an aqueous solution having a volume of about 5 mL or less. In another embodiment, the drug reservoir can accommodate an aqueous solution having a volume of about 4 mL or less. In yet another embodiment, the drug reservoir can accommodate an aqueous solution having a volume of about 3 mL or less. In still another embodiment, the drug reservoir can accommodate an aqueous solution having a volume of about 2 mL or less. In yet still another embodiment, the drug reservoir can accommodate an aqueous solution having a volume of about 1 mL or less.

Breath Actuation

In certain embodiments, the aerosol therapy device described herein can be turned on by the user manually while the soft palate is closed by the patient. Closure of the soft palate during aerosol delivery isolates the nasal and paranasal chambers. This ensures minimal delivery of the aerosol to the lungs and increases the potential for aerosol deposition in the sinuses.

In certain embodiments, the aerosol generator and pulsated air generator are triggered when the patient breathes into an exhalation triggering device. In one embodiment, the triggering device is in the form of a mouthpiece. In another embodiment, the triggering device is mouthpiece physically connected to the aerosol therapy device components to yield a compact design. In other embodiments, the mouthpiece can be detachable and replaceable.

In certain embodiments, the exhalation triggering device further comprises a restrictor to create pressure resistance, thereby controlling the relative exhalation speed. The relative exhalation speed will affect the length the device is actuated to accommodate different delivery times for various patients, such as a child or adult, or based on the type of disease and treatment regime. In one embodiment, the flow restriction is achieved by a small hole on the surface of the mouthpiece, thereby limiting the amount of air entering the exhalation triggering device. In this embodiment, the relative exhalation speed can be altered by swapping the removable mouthpiece with one with a different hole size. In other embodiments, the flow restriction can be achieved by placing a flow restrictor inside the exhalation triggering device and having a one way flow valve to provide ease of inhalation. In one embodiment, the flow restrictor comprises a plate with a precision machined hole. In this embodiment, the size and/or quantity of holes can be altered to achieve different flow rates and/or increased control. In one embodiment, the flow restrictor is removable and swapped with a different flow restrictor with a different flow rate. In other embodiments, the flow rate is adjustable by the user without removing the flow restrictor by means commonly known to one skilled in the art, for example a set-screw or orifice closing mechanism with an accessible control knob. The flow restrictors can be made from a variety of metals, metal alloys, and thermoplastics generally known in the art.

In certain aspect of the present invention, the breath trigger can comprise a sensor for detecting any suitable parameter such as gas flow, pressure, temperature, sound, moisture, carbon dioxide concentration and oxygen concentration. Many suitable sensors are envisaged including the use of optical sensors, mechanical sensors, flow transducers, thermal sensors, gas detectors, and motion detectors. In one embodiment, the sensor is a mechanical device, for example, a pivoted vane, which moves to close a switch when there is an air flow through the mouth piece. In another embodiment, the sensor is an optical sensor, such as an infrared sensor, which measures the gas content inside the exhalation triggering device. The signal from the exhalation triggering device is transmitted to the aerosol therapy device for actuation. In certain embodiments, the signal is transmitted to an electronic data management system, which then controls the aerosol therapy device.

In one embodiment, an electronic data management system can be utilized, which comprises a microprocessor and predictive algorithm or look-up table for deriving from the breath data when to transmit the trigger signal. In other embodiments, a real-time analysis of the patient breath waveform may be made and the trigger point derived by reference to that analyzed waveform. In still other embodiments, the algorithm contains a time delay for triggering the aerosol therapy device.

In certain embodiments, the exhalation triggering device can further comprise a one way valve to restrict the air flow within the triggering device to one direction. In other embodiment, the mouthpiece further comprises an inhalation tube or pathway for increased air intake peripheral to the exhaling pathway.

Delivery Times

In certain embodiments of the aerosol therapy device described herein, the aerosol therapy device can deliver the aqueous solution comprising the active agent in about 10 minutes or less. In one embodiment, the aerosol therapy device can deliver the aqueous solution comprising the active agent in about 5 minutes or less. In another embodiment, the aerosol therapy device can deliver the aqueous solution comprising the active agent in about 4 minutes or less. In yet another embodiment, the aerosol therapy device can deliver the aqueous solution comprising the active agent in about 3 minutes or less. In still another embodiment, the aerosol therapy device can deliver the aqueous solution comprising the active agent in about 2 minutes or less.

Active Agents

The aerosol therapy device described herein can be used to deliver a variety of different active agents. Any drug or active agent that can be provided as an aqueous drug, including but not limited to, a solution, dispersion, emulsion, colloidal liquid, micelle or mixed micelle liquid, liposomal liquid, nano-suspension, or a suspension can be delivered as an active agent via the aerosol therapy device set forth herein, which offers the possibility of topical drug delivery to the nasal mucosa and/or systemic drug delivery via the nasal sinuses, depending on the particle size distribution achieved. In certain embodiments, the aerosol therapy device described herein can be used to deliver neurologic agents to the brain or central nervous system to treat disorders or diseases of neurological etiology. In still other embodiments, the aerosol therapy device described herein can be used to deliver vaccines designed for aerosol and/or nasal delivery.

In particular, the aerosol therapy device described herein enables enhanced delivery of active agents to the paranasal sinuses for the treatment of disorders including, but not limited to, acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis).

In one embodiment, acute sinusitis is treated by active agents delivered to the paranasal sinus according to the present invention. In another embodiment, chronic sinusitis is treated by active agents delivered to the paranasal sinus according to the present invention. In yet another embodiment, illnesses such as fungal allergic sinusitis, inflammations or other infections or conditions such as atrophic rhinitis can also be topically treated by the present invention. In certain embodiments, allergic rhinitis such as seasonal allergic rhinitis and perennial allergic rhinitis are treated by the present invention. In other embodiments, the present invention can be used for treatment of fungal sinusitis such as mycetoma fungal sinusitis, allergic fungal sinusitis, chronic indolent sinusitis, and fulminant sinusitis.

In other embodiments, diseases of the upper and lower respiratory tract can be directly treated therewith if they have a nasal or paranasal cause. In certain embodiments, the respiratory disease to be treated can be upper respiratory tract infection, common cold, pharyngitis, tonsillitis, laryngitis, tracheitis, croup, epiglottitis, influenza, pneumonia influenza, severe acute respiratory syndrome, bronchitis, bronchiolitis, vasomotor rhinitis, deviated septum, adenoid hypertrophy, peritonsillar abscess, vocal fold nodule, laryngospasm, emphysema, COPD, asthma, status asthmaticus, and bronchiectasis. In yet other embodiments, the present invention can be used for treatment of headaches, pain and pressure around the eyes, achy feeling in the upper teeth, fever and chills, facial swelling, nasal stuffiness or congestion, and yellow or green discharge.

Systemic delivery utilizing the nasal mucosa and mucosa in the paranasal sinuses is desired for many other targeted disease states. Examples of diseases that can be treated by systemic delivery with the present invention includes, but are not limited to, endocrine and metabolic disorders, migraines, sleep disorders, autoimmune diseases, osteoporosis, neurological diseases and disorders, pain, nausea and vomiting, obesity, sexual dysfunctions, cardiovascular diseases and episodes, herpes, sarcoidosis, fibrosis, cancer, or autoimmune reaction.

In particular, the aerosol therapy device described herein can enable enhanced delivery of active agents to the CNS through the olfactory pathway for the treatment of disorders including, but not limited to, Alzheimer's disease, Huntington's disease, migraine, Parkinson's disease, nerve damage from cerebrovascular disorders and stroke and ordinary aging, affective disorders such as depression and mania, loss of smell, epilepsy, emesis, erectile dysfunction, hemophilia A, central precocious puberty, allergies, seizures, myasthenia gravis, hypertension, angina pectoris, polydepsia, polyurea, and diabetes.

For a user with a secondary condition of nasal polyps, the present invention provides effective application of the medicine, which is otherwise blocked or precluded using contemporary systems. The present invention is significantly more effective in slowing polyp re-growth following their removal by administering, for example, corticosteroids to slow the re-growth. The present invention also provides effective application for tumors and cancers, such as nasal cavity and paranasal sinus cancers.

In certain embodiments, the surface tension of the aqueous drug solution can be between about 10 to 70 dynes/cm, in order to yield an aerosol having the target aerosol particle diameter. In certain aspects, the surface tension of the aqueous drug solution can be between about 20 to 60 dynes/cm, in order to yield an aerosol having the target aerosol particle diameter. In other aspects, the surface tension of the aqueous drug solution can be between about 30 to 50 dynes/cm, in order to yield an aerosol having the target aerosol particle diameter. Surface tension of a given formulation may be adjusted by adding a surfactant. In certain embodiments, the solution can have a pH in the range of about 3.0 to 8.5, an osmotic pressure between about 150 mOsm/kg to 880 mOsm/kg, and a NaCl equivalency between about 0.9% NaCl to 3.0% NaCl.

Of the active ingredients which can be of some use for attaining one of these targets are e.g. substances which can be selected from the group of anti-inflammatory drugs, glucocorticoids, anti-infective agents, antibiotics, anti-emetics, fungicides, virucides either alone or in combination with biofilm-reducing compounds or inhibitors of efflux pumps, antiseptics, neurological agents, immunomodulators, antioxidants, mycolytica, decongestives, vasoconstrictors, non-steroidal anti-inflammatory drugs (NSAIDs), wound-treatment agents, local anesthetics, peptides, proteins and natural or synthetic plant extracts.

Examples of potentially useful anti-inflammatory drugs, include but are not limited to, steroidal active ingredients such as glucocorticoids such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate and non-steroidal anti-inflammatory drugs (NSAIDs) such as prostaglandins, leukotriene, elastane, bradykinin antagonists, heparin and heparinoide, non-glucocorticoid steroids such as dehdroepiundrostendieone and dehdropianthrosterone (DHEA); any pharmaceutically acceptable salts, esters, isomers, stereoisomers, diastereomers, epimers, solvates or other hydrates, prodrugs, derivates or any other chemical or physical forms of the active ingredients which include the corresponding active units.

Examples of anti-infective agents, the class or therapeutic category of which being understood here such that they include, but are not limited to, compounds which are effective against bacterial, fungoid and viral infections, i.e. that they include the classes of antimicrobial substances, the antibiotics, fungicides, antiseptics and virucides, either alone or in combination with biofilm-reducing or repressive agents and inhibitors of the efflux pump, are penicillins including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillin (mecillinam); cefalosporins including cefazolins (cefazolin, cefazedone); cefuroximes (cerufoxim, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulan acid, amoxicillin, ceftobiprole; synergists including beta-lactamase inhibitors, such as clavulan acids, sulbactam and tazobactam; cabapenems including imipenem, cilastin, meropenem, doripenem, tebipenem, ertapenem, ritipenam, and biapenem; monobactams including aztreonam; aminoglycosides such as apramycin, gentamicin, amikacin, isepamicin, arbekacin, tobramycin, netilmicin, spectinomycin, streptomycin, capreomycin, neomycin, paromoycin and kanamycin; macrolides including erythromycin, clarythromycin, roxithromycin, azithromycin, dithromycin, josamycin, spiramycin and telithromycin; gyrase inhibitors or fluroquinolones including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin and moxifloxacin; tetracycline including tetracyclin, oxytetracyclin, rolitetracyclin, minocyclin, doxycycline, tigecycline and aminocycline; glycopeptide including vancomycin, teicoplanin, ristocetin, avoparcin, oritavancin, ramoplanin and Peptid 4; polypeptides including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides including sulfadiazine, sulfamethoxazole, sulfalene, co-trimoxazole, co-trimetrol, co-trimoxazine, co-tetraxazine; azoles including clotrimazole, oxiconazole, miconazole, ketoconazole, itraconazole, fluconazole, metronidazol, tinidazol, bifonazol, ravuconazol, posaconazol, voriconazol and ornidazol and other fungicides including flucytosin, griseofluvin, tonoftal, naftifin, terbinafin, amorolfin, ciclopiroxolamin, echinocundins, such as micafungin, caspofungin, anidulafungin; nitrofurans including nitrofurantoin and nitrofuranzon; polyenes including amphotericin B, natamycin, nystatin, flucocytosin; other antibiotics including tithromycin, lincomycin, clindamycin, oxazolindione (linzezolide), ranbezolid, streptogramin A+B, pristinamycin aA+B, virginiamycin A+B, dalfopristin/giunupristin (synercide), chloramphenicol, ethambutol, pyrazinamid, terizidon, dapson, prothionamid, fosfomycin, fucidinic acid, rifampicin, isoniazide, cycloserine, terizidone, ansamycine, lysostaphin, iclaprim, mirocin B17, clerocidine, filgrastim, and pentamidin; virucides including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabin, tromantadin and proteinase inhibitors; antiseptics including acridine derivatives, iodine providon, benzoates, rivanol, chlorohexetidine, quarternary ammonium compounds, cetrimides, biphenylol, clorofene and octenidine; plant extracts or components, such as plant extracts of chamomile, hamamelis, echiancea, calendula, papain, pelargonium, essential oils, myrtol, pinene, limonene, cineole, thymol, menthol, camphor, tannin, alpha-hederin, bisabol oil, lycopodin, vitapher oil;

Wound-treatment compounds for use with the aerosol therapy device described herein include, but are not limited to, dexpanthenol, allantoin, vitamins, hyaluronic acid, alpha-antitrypsin, inorganic and organic zinc salts/compounds, bismuth salts, interferons (alpha, beta, gamma), tumor necrosis factors, cytokines, interleukines, immunomodulators including methotrexat, azathioprin, cyclosporin, tacrolimus, sirolimus, rapamycin, mofetil, cytostatic agents and metastases inhibitoren, alkylants, such as nimustin, melphanlan, carmustin, lomustin, cyclophosphamide, ifosfamide, trofosfamide, chloroambucile, busulfan, treosulfan, prednimustin, thiotepa;

Anti-metabolites for use with the aerosol therapy device described herein, include but are not limited to, cytarabin, fluorouracil, methotrexat, mercaptopurin, tioguanin; alkaloids such as vinblastin, vincristin, vindesin; antibiotics such as alcarubicin, bleomycin, dactinomycin, daunorubicin, doxorubicin, epirubicin, idarubicin, mitomycin, plicamycin; complexes of two-group elements (e.g. Ti, Zr, V, Nb, Ta, Mo, W, Pt) such as carboplatinim, cis-platinum and metallocen compounds such as titanocen dichloride; amsacrin, dacarbazin, estramustin, etoposide, beraprost, hydroxycarbamide, mitoxanthron, procarbazin, temiposide; paclitaxel, iressa, zactima, poly-ADP-ribose-polymerase (PRAP) enzyme inhibitors, banoxantron, gemcitabin, pemetrexed, bevacizumab, ranibizumab.

Examples of potentially useful mycolytics include, but are not limited to, DNase, P2Y2-agonists (denufosol), heparinoides, guaifenesin, acetylcystein, carbocystein, aambroxol, bromhexin, tyloxapol, lecithine, myrtol, and recombined surfactant proteins.

Examples of potentially useful vasoconstrictors which can be useful to reduce swelling of the mucous membrane include, but are not limited to, phenylephrine, naphazoline, tramazoline, tetryzoline, oxymetazoline, fenoxazoline, xylometazoline, epinephrine, isoprenaline, hexoprenaline and ephedrine.

Examples of potentially useful local anesthetics include, but are not limited, tobenzocaine, tetracaine, procaine, lidocaine and bupivacaine.

Examples of potentially useful anti-emetics for the treatment of nausea and vomiting include, but are not limited to, 5-HT receptor agonists (e.g., dolasetron and palonosetron), dopamine agonists (e.g., domperidone an alizapride), anti-histamines, cannabinoids, bensodiazepines (e.g., midazolam and larazepam), and anti-cholinergic agents (e.g., scopolamine).

Examples of potentially useful neurologic agents which can be useful for treatment to the CNS through the olfactory pathway include but are not limited to melanocortin-4 receptor, nerve growth factor, ganglioside, phosphatidylserine, brain-derived neurotrophic factor, fibroblast growth factor, insulin, insulin-like growth factors, ciliary neurotrophic factor glia-derived nexin, cholinergic enhancing factors such as phosphoethanolamine and thyroid hormone T.3, thyrotropin-releasing hormone and analogues, endogenous central nervous system tripeptide, butorphanol tartarate, desmopressin acetate, nafarelin acetate, DHE-45 dihydroergotamine, zolmitriptan, scopolamine hydrobromide, buprenorphine hydrochloride, chlorpheniramine maleate, chlorphenyridamine maleate, prophenpyridamine maleate, clonazepam, diphenylhydramine hydrochloride, doxylamine succinate, ergotamine tartarate, metoclopramide hydrochloride, midazolam, neostigmine bromide, nicotine, propanolol hydrochloride, sufentil citrate, and vasopressin. Examples of potentially useful agents for enhanced penetration of the blood brain barrier for delivery to the CNS include but are not limited to surfactants, betacyclodextrins, bile salts, phospholipids, and/or lysophospholipids.

Examples of potentially useful local antiallergics include but are not limited to the above-mention glucocorticoids, cromolyn sodium, nedocromil, cetrizin, loratidine, montelukast, roflumilast, ziluton, omalizumab and heparinoids.

Examples of potentially useful peptides and proteins contain antibodies produced from microorganisms against toxins, antimicrobial peptides such as cecropine, defensine, thionine and cathelicidine.

Combinations of any of the above-mentioned active ingredients, which consist of any pharmaceutically acceptable salt, ester, isomer, stereoisomer, diastereomer, epimer, solvate or other hydrate, prodrugs, derivative or any other chemical or physical form of active ingredients, which include the corresponding active units.

The aforementioned substances are preferably used in the form of their common pharmaceutical configurations or as salts, esters, isomers, stereoisomers, diastereomers, epimers, etc., with the objective being in each case to obtain an administrative form that it stable when stored. For this, formulations may be used in a wide variety of administrative forms, for example as solutions, suspensions, emulsions, powders or lyophilisates, etc. in 2-chamber systems with aqueous or non-aqueous solvents or mixtures, etc. It is advantageous to add excipients that improve solubility, for example glycerol, propylene glycol, ethanol, encourage penetration of the paranasal sinuses and frontal sinuses, reduce surface tension and/or prolong the deposition time and dwell time (control release) where appropriate, which may be achieved, for example, by the addition of non-ionic surfactants, for example tyloxapol, vitamin E-TPGS, polysorbates, pluronics, etc. and/or other additives as for example phospholipids, cellulose ether, dextrans, chitosans, cyclodextrines, polyvinylpyrrolidone, polyvinyl alcohol, etc.

Also claimed as inventive is the formulation and application of the aforementioned classes of active ingredients and substances as liposomes, suspensions and emulsions in the micrometer range and preferably in the nanometer range with a geometric diameter of less than approximately 1 μm that are particularly suitable for transportation by small droplets. This ensures that by means of the device according to the invention these preparations are better able to penetrate the paranasal sinuses and frontal sinuses and be deposited and hence develop their action. Active ingredients that have to be used as solid formulations due to their poor storage stability in solution may be either dissolved or suspended with a suitable aqueous or non-aqueous solvent (for example glycerol, propylene glycol, polyglycols, pluronics, ethanol) or mixtures thereof shortly before application. Also claimed is a coating and encasing method to make malodorous or locally irritant substances more tolerable for application by complexation, for example with cyclodextrins. Alternatively, these active ingredients may also be bonded to polymeric excipients, for example chitosan and cellulose ether derivatives or gelatins in order to modify the absorption properties in such a way that the therapeutic effect may be intensified and the application frequency reduced. It is advantageous to use isotonic or hypertonic solutions containing soluble alkali and alkaline-earth salts (for example Emser salts, magnesium chloride, sodium hydrogen carbonate, etc.) and have a physiological pH range (4-9). This may be achieved by the addition of common pharmaceutical buffer substances to the active ingredient formulations. The formulations may also be provided with pharmaceutically common aroma and taste correcting agents to improve their acceptance, particularly as far as children are concerned.

Further contemplated by the present invention is the use of the aerosol therapy device described herein to enable enhanced delivery of vaccines designed for aerosol and/or nasal delivery for the prevention of certain diseases or disorders including, but not limited to, influenza, tuberculosis, measles, and HIV/AIDS.

EXAMPLES

The present invention is further illustrated by the following examples, which should not be construed as limiting in any way. The experimental procedures to generate the data shown are discussed in more detail below. The invention has been described in an illustrative manner, and it is to be understood that the terminology used is intended to be in the nature of description rather than of limitation.

Example 1

Parametric Deposition Test

A nasal cast model is made of silicone with sinuses being represented by four cylindrical chambers of equal volume.

The ostia diameter is varied from 0.5 mm to 3 mm and the size of the chambers is altered from 5 to 25 mL. A 1% NaF tracer solution is deposited as an aerosol into the nasal cast using the aerosol therapy device of present invention.

The nasal cast is disassembled and the tracer solution is washed from each individual part for potentiometric analysis. The whole amount of aerosol deposited in the sinus cavities is calculated form the sum of the single cavities (sum of sinuses).

The ostium size, resonance frequency of the pulsating air flow, pressure of the pulse, chamber size, and the mass median particle size are altered in varying combinations. The deposition amount is measured by potentiometric analysis and compared.

Example 2

Technetium Imaging Test

A nasal cast similar to Example 1 is used. Scintigraphic images are performed of the models in above, face, and profile views using a technetium ($^{99m}$Tc)-labeled solution, which is deposited as an aerosol into the nasal cast using the aerosol therapy device of present invention. The aerosol therapy device generates a single airflow consisting of a pulsating flow of air comprising an acoustic pressure field ranging from about 15 to about 40 mbar, wherein the airflow pulsates at a frequency of about 800 Hz.

The radioactivity deposited on gauze compresses placed inside the maxillary sinuses is counted. The results confirm that aerosols which are delivered from the aerosol therapy device can reach the maxillary sinuses, which is one of the primary areas for sinusitis disorders.

Example 3

Paranasal Deposition Testing Using an Endoscopic Sinus Surgery Model

A human paranasal model developed for Endoscopic Sinus Surgery (ESS) training (ESS Basic Set, SurgiTrainer, Ltd., Ibaraki, Japan) is used to evaluate the paranasal sinus deposition of a 1% NaF tracer solution, which is deposited as an aerosol into the nasal cast using the aerosol therapy device of present invention. The aerosol therapy device generates a single airflow consisting of a pulsating flow of air comprising an acoustic pressure field ranging from about 15 to about 40 mbar, wherein the airflow pulsates at a frequency of about 800 Hz.

The human paranasal model is disassembled and the tracer solution is washed from each individual part for potentiometric analysis. The whole amount of aerosol deposited in the sinus cavities is calculated from the sum of the single cavities (e.g., maxillary, sphenoid, ethmoid and frontal sinuses).

The deposition amount is measured by potentiometric analysis and compared. These results confirm that aerosols which are delivered from the aerosol therapy device can reach the middle meatus, which is one of the primary areas for sinusitis disorders.

What is claimed is:

1. An aerosol therapy device for delivery of an active agent to the paranasal sinuses of a patient comprising:
    (a) an aqueous drug reservoir, said aqueous drug reservoir being connected to
    (b) an aerosol generator for the generation of aerosol particles, said aerosol generator being connected to
    (c) an air-flow supply device, said air-flow supply device producing a single airflow to carry said aerosol particles of (b), wherein said single airflow consists of a pulsating flow of air and comprises a pressure field produced by a pulsed pressure wave, wherein said pulsating airflow pulsates at a frequency from about 150 Hz to about 6000 Hz; and
    (d) a nosepiece to direct said single airflow comprising aerosol particles of (c) into one of the two alae of the nose of the patient wherein said nose piece is a twin-port nose piece,
    whereby said aerosol therapy device delivers aerosol particles comprising an active agent to the paranasal sinuses of the patient.

2. The aerosol therapy device of claim 1, wherein said air-flow supply device of (c) is selected from a mechanical pump, and pneumatic pump or an electric pump.

3. The aerosol therapy device of claim 1, wherein said air-flow supply device of (c) is a mechanical pump.

4. The aerosol therapy device of claim 1, wherein said air-flow supply device of (c) is a pneumatic pump.

5. The aerosol therapy device of claim 1, wherein said air-flow supply device of (c) is an electric pump.

6. The aerosol therapy device of claim 5, wherein said air-flow supply device of (c) is a piezoelectric pump.

7. The aerosol therapy device of claim 1, wherein said aerosol generator of (b) is selected from the group consisting of a pulsating membrane device, a device comprising a vibrating mesh or plate with multiple apertures, a thin-film resistive heater with a diaphragm membrane, or a device comprising a vibration generator.

8. The aerosol therapy device of claim 1, wherein said aerosol particles have a mass-median aerodynamic diameter (MMAD) of from about 0.5 µm to about 150.0 µm, from about 20 µm to about 150.0 µm, from about 0.5 µm to about 10 µm, from 5 µm to about 20 µm, from about 20 µm to about 150 µm, from about 20 µm to about 50 µm, or from about 50 µm to about 150 µm.

9. The aerosol therapy device of claim 1, wherein said aerosol particles have a mass-median aerodynamic diameter (MMAD) of from about 2.0 µm to about 8.0 µm.

10. The aerosol therapy device of claim 1, wherein said aerosol particles have a mass-median aerodynamic diameter (MMAD) of from about 3.0 µm to about 5.0 µm.

11. The aerosol therapy device of claim 1, wherein said pressure field of (c) is an acoustic pressure field.

12. The aerosol therapy device of claim 1, wherein said pulsating airflow pulsates at a frequency from about 300 Hz to about 4000 Hz.

13. The aerosol therapy device of claim 1, wherein said pulsating airflow pulsates at a frequency from about 500 Hz to about 3000 Hz.

14. The aerosol therapy device of claim 1, wherein said pulsating airflow pulsates at a frequency from about 150 Hz to about 1100 Hz.

15. The aerosol therapy device of claim 1, wherein said single airflow consists of a pulsating flow of air comprises a pressure field ranging from about 5 to about 50 mbar.

16. The aerosol therapy device of claim 1, wherein said single airflow consists of a pulsating flow of air comprises a pressure field ranging from about 15 to about 40 mbar.

17. The aerosol therapy device of claim 1, wherein said single airflow consists of a pulsating flow of air comprises a pressure field ranging from about 15 to about 30 mbar.

18. The aerosol therapy device of claim 1, wherein said device delivers a therapeutically effective dose of an active agent to the paranasal sinuses in less than about 10 minutes.

19. The aerosol therapy device of claim 1, wherein said device delivers a therapeutically effective dose of an active agent to the paranasal sinuses in less than about 5 minutes.

20. The aerosol therapy device of claim 1, wherein said device delivers a therapeutically effective dose of an active agent to the paranasal sinuses in less than about 4 minutes.

21. The aerosol therapy device of claim 1, wherein said device delivers a therapeutically effective dose of an active agent to the paranasal sinuses in less than about 3 minutes.

22. The aerosol therapy device of claim 1, wherein said device delivers a therapeutically effective dose of an active agent to the paranasal sinuses in less than about 2 minutes.

23. The aerosol therapy device of claim 1, wherein said device delivers a therapeutically effective dose of an active agent to the paranasal sinuses in less than about 1 minute.

24. The aerosol therapy device of claim 1, wherein said active agent is an aqueous formulation having a volume of less than about 5 mls.

25. The aerosol therapy device of claim 1, wherein said active agent is an aqueous formulation having a volume of less than about 4 mls.

26. The aerosol therapy device of claim 1, wherein said active agent is an aqueous formulation having a volume of less than about 3 mls.

27. The aerosol therapy device of claim 1, wherein said active agent is an aqueous formulation having a volume of less than about 2 mls.

28. The aerosol therapy device of claim 1, which further comprises a breath trigger or a breath actuator.

29. The aerosol therapy device of claim 1, wherein said airflow comprising aerosol particles of (c) is directed into one of the two alae of the nose in an alternating fashion.

30. The aerosol therapy device of claim 29, wherein said alternating airflow alternates between said one of the two alae at 30 second intervals.

31. The aerosol therapy device of claim 1, wherein in said device is self-tuning.

32. The aerosol therapy device of claim 1, wherein said device can sweep a range of frequencies to determine the optimum pulsating frequency to obtain delivery of said active agent to the paranasal sinuses.

33. The aerosol therapy device of claim 32, wherein said device sweeps a range of frequencies from about 150 Hz to about 6000 Hz.

34. The aerosol therapy device of claim 32, wherein said device sweeps a range of frequencies from about 150 Hz to about 2500 Hz.

35. The aerosol therapy device of claim 32, wherein said device sweeps a range of frequencies from about 300 Hz to about 4000 Hz.

36. The aerosol therapy device of claim 32, wherein said device sweeps a range of frequencies from about 500 Hz to about 3000 Hz.

37. A method of treating sinusitis using the aerosol therapy device of claim 1, wherein said active agent is selected from the group consisting of anti-inflammatory drugs, glucocorticoids, anti-infective agents, antibiotics, and fungicides.

38. An aerosol therapy device for intranasal delivery of an active agent to the central nervous system via the olfactory region of the nasal passages to a patient in need thereof comprising:
  (a) an aqueous drug reservoir, said aqueous drug reservoir being connected to
  (b) an aerosol generator for the generation of aerosol particles, said aerosol generator being connected to
  (c) an air-flow supply device, said air-flow supply device producing a single airflow to carry said aerosol particles of (b), wherein said single airflow consists of a pulsating flow of air and comprises a pressure field produced by a pulsed pressure wave, wherein said pulsating airflow pulsates at a frequency from about 150 Hz to about 6000 Hz; and
  (d) a twin-port nosepiece to simultaneously direct said single airflow comprising aerosol particles of (c) into both alae of the nose of the patient,
  whereby said aerosol therapy device intranasally delivers aerosol particles comprising an active agent to the olfactory region of the nasal passages of the patient.

39. A method of treating a disorder of the central nervous system using the aerosol therapy device of claim 38, wherein said active agent is selected from the group consisting of melanocortin-4 receptor, nerve growth factor, ganglioside, phosphatidylserine, brain-derived neurotrophic factor, fibroblast growth factor, insulin, insulin-like growth factors, ciliary neurotrophic factor glia-derived nexin, cholinergic enhancing factors such as phosphoethanolamine and thyroid hormone T.3, thyrotropin-releasing hormone and analogues, endogenous central nervous system tripeptide, butorphanol tartrate, desmopressin acetate, nafarelin acetate, DHE-45 dihydroergotamine, zolmitriptan, scopolamine hydrobromide, buprenorphine hydrochloride, chlorpheniramine maleate, chlorphenpyridamine maleate, prophenpyridamine maleate, clonazepam, diphenylhydramine hydrochloride, doxylamine succinate, ergotamine tartarate, metoclopramide hydrochloride, midazolam, neostigmine bromide, nicotine, propanolol hydrochloride, sufentil citrate, and vasopressin.

40. An aerosol therapy device for systemic delivery of an active agent to the nasal passages and/or sinuses of a patient in need thereof comprising:
  (a) an aqueous drug reservoir, said aqueous drug reservoir being connected to
  (b) an aerosol generator for the generation of aerosol particles, said aerosol generator being connected to
  (c) an air-flow supply device, said air-flow supply device producing a single airflow to carry said aerosol particles of (b), wherein said single airflow consists of a pulsating flow of air and comprises a pressure field produced by a pulsed pressure wave, wherein said pulsating airflow pulsates at a frequency from about 150 Hz to about 6000 Hz; and
  (d) a twin-port nosepiece to direct said single airflow comprising aerosol particles of (c) into one or both alae of the nose of the patient,
  whereby said aerosol therapy device delivers aerosol particles comprising an active agent to the nasal passages and/or sinuses of the patient.

41. A method for the systemic delivery of an active agent for the treatment of a disorder using the aerosol therapy device of claim 40, wherein said disorder is selected from endocrine and metabolic disorders, migraines, sleep disorders, autoimmune diseases, osteoporosis, neurological diseases and disorders, pain, nausea and vomiting, obesity, sexual dysfunctions, cardiovascular diseases and episodes, herpes, sarcoidosis, fibrosis, cancer, or autoimmune reaction.

* * * * *